United States Patent
Schultheis et al.

(10) Patent No.: US 11,839,391 B2
(45) Date of Patent: Dec. 12, 2023

(54) OPTICAL EMITTER HOUSING ASSEMBLY FOR INTRAVASCULAR LITHOTRIPSY DEVICE

(71) Applicant: BOLT MEDICAL, INC., Carlsbad, CA (US)

(72) Inventors: Eric Schultheis, San Clemente, CA (US); Alvin Salinas, San Marcos, CA (US); Alan Duong, San Diego, CA (US)

(73) Assignee: Bolt Medical, Inc., Carlsbad, CA (US)

( * ) Notice: Subject to any disclaimer, the term of this patent is extended or adjusted under 35 U.S.C. 154(b) by 0 days.

(21) Appl. No.: 17/970,363

(22) Filed: Oct. 20, 2022

(65) Prior Publication Data

US 2023/0181254 A1 Jun. 15, 2023

Related U.S. Application Data

(60) Provisional application No. 63/335,131, filed on Apr. 26, 2022, provisional application No. 63/289,294, filed on Dec. 14, 2021.

(51) Int. Cl.
*A61B 18/20* (2006.01)
*A61B 17/22* (2006.01)
(Continued)

(52) U.S. Cl.
CPC ........ *A61B 17/22022* (2013.01); *A61B 18/24* (2013.01); *A61B 2017/22021* (2013.01);
(Continued)

(58) Field of Classification Search
CPC ...... A61B 18/24; A61B 18/26; A61B 2018/26
See application file for complete search history.

(56) References Cited

U.S. PATENT DOCUMENTS

| 4,649,924 A | 3/1987 | Taccardi |
| 4,699,147 A | 10/1987 | Chilson et al. |

(Continued)

FOREIGN PATENT DOCUMENTS

| AU | 2017205323 | 1/2022 |
| AU | 2019452180 | 1/2022 |

(Continued)

OTHER PUBLICATIONS

International Preliminary Report on Patentability dated Sep. 15, 2020 in PCT Application Serial No. PCT/US2019/022009.
(Continued)

*Primary Examiner* — Lynsey C Eiseman
(74) *Attorney, Agent, or Firm* — ROEDER & BRODER LLP; James P. Broder

(57) ABSTRACT

A catheter system (100) for treating a treatment site (106) within or adjacent to a vessel wall (108A) of a blood vessel (108) within a body (107) of a patient (109) includes an energy source (124), a catheter fluid (132), and an emitter assembly (129). The energy source (124) generates energy. The emitter assembly (129) includes (i) at least a portion of an energy guide (122A) having a guide distal end (122D) that is selectively positioned near the treatment site (106), (ii) a plasma generator (133), and (iii) an emitter housing (260) that is secured to each of the energy guide (122A) and the plasma generator (133) to maintain a relative position between the guide distal end (122D) of the energy guide (122A) and the plasma generator (133). The energy guide (122A) is configured to receive energy from the energy source (124) and direct the energy toward the plasma generator (133) to generate a plasma bubble (134) in the catheter fluid (132). The plasma generator (133) directs energy from the plasma bubble (134) toward the treatment site (106).

20 Claims, 6 Drawing Sheets

(51) Int. Cl.
  *A61B 18/24*   (2006.01)
  *A61B 18/00*   (2006.01)
  *A61B 18/26*   (2006.01)

(52) U.S. Cl.
  CPC .............. *A61B 2017/22025* (2013.01); *A61B 2017/22038* (2013.01); *A61B 2018/0022* (2013.01); *A61B 2018/00404* (2013.01); *A61B 2018/263* (2013.01)

(56) References Cited

U.S. PATENT DOCUMENTS

| | | |
|---|---|---|
| 4,799,479 A | 1/1989 | Spears |
| 4,913,142 A | 4/1990 | Kittrell et al. |
| 4,932,954 A | 6/1990 | Wondrazek et al. |
| 4,955,895 A | 9/1990 | Suglyama |
| 4,960,108 A | 10/1990 | Reichel et al. |
| 4,994,059 A | 2/1991 | Kosa et al. |
| 5,034,010 A | 7/1991 | Kittrell et al. |
| 5,041,121 A | 8/1991 | Wondrazek et al. |
| 5,082,343 A | 1/1992 | Coult et al. |
| 5,093,877 A | 3/1992 | Aita et al. |
| 5,104,391 A | 4/1992 | Ingle |
| 5,104,392 A | 4/1992 | Kittrell et al. |
| 5,116,227 A | 5/1992 | Levy |
| 5,152,768 A | 10/1992 | Bhatta |
| 5,173,049 A | 12/1992 | Levy |
| 5,181,921 A | 1/1993 | Makita et al. |
| 5,200,838 A | 4/1993 | Nudelman |
| 5,290,277 A | 3/1994 | Vercimak et al. |
| 5,324,282 A | 6/1994 | Dodick |
| 5,372,138 A | 12/1994 | Crowley |
| 5,387,225 A | 2/1995 | Euteneur |
| 5,400,428 A | 3/1995 | Grace |
| 5,422,926 A | 6/1995 | Smith |
| 5,454,809 A | 10/1995 | Janssen |
| 5,509,917 A | 4/1996 | Cecchetti |
| 5,540,679 A | 7/1996 | Fram |
| 5,562,657 A | 10/1996 | Griffin |
| 5,598,494 A | 1/1997 | Behrmann et al. |
| 5,609,606 A | 3/1997 | O'Boyle |
| 5,611,807 A | 3/1997 | O'Boyle |
| 5,697,377 A | 12/1997 | Wittkamph |
| 5,718,241 A | 2/1998 | Ben-Haim et al. |
| 5,729,583 A | 3/1998 | Tang |
| 5,772,609 A | 6/1998 | Nguyen et al. |
| 5,860,974 A | 1/1999 | Abele |
| 5,891,135 A | 4/1999 | Jackson et al. |
| 5,906,611 A | 5/1999 | Dodick et al. |
| 5,944,697 A | 8/1999 | Benett et al. |
| 6,015,404 A | 1/2000 | Altshuler |
| 6,080,119 A | 6/2000 | Schwarze et al. |
| 6,123,923 A | 9/2000 | Unger |
| 6,139,510 A | 10/2000 | Palermo |
| 6,186,963 B1 | 2/2001 | Schwarze et al. |
| 6,203,537 B1 | 3/2001 | Adrian |
| 6,210,404 B1 | 4/2001 | Shadduck |
| 6,339,470 B1 | 1/2002 | Papademetriou et al. |
| 6,356,575 B1 | 3/2002 | Fukumoto |
| 6,368,318 B1 | 4/2002 | Visuri et al. |
| 6,500,174 B1 | 12/2002 | Maguire et al. |
| 6,514,203 B2 | 2/2003 | Bukshpan |
| 6,514,249 B1 | 2/2003 | Maguire |
| 6,524,251 B2 | 3/2003 | Rabiner et al. |
| 6,538,739 B1 | 3/2003 | Visuri et al. |
| 6,607,502 B1 | 8/2003 | Maguire et al. |
| 6,652,547 B2 | 11/2003 | Rabiner et al. |
| 6,666,834 B2 | 12/2003 | Restle et al. |
| 6,773,447 B2 | 8/2004 | Laguna |
| 6,849,994 B1 | 2/2005 | White et al. |
| 6,947,785 B1 | 9/2005 | Beatty et al. |
| 6,978,168 B2 | 12/2005 | Beatty et al. |
| 6,990,370 B1 | 1/2006 | Beatty et al. |
| 7,309,324 B2 | 12/2007 | Hayes et al. |
| 7,470,240 B2 | 12/2008 | Schultheiss et al. |
| 7,539,231 B1 | 5/2009 | Honea et al. |
| 7,569,032 B2 | 8/2009 | Naimark et al. |
| 7,599,588 B2 | 10/2009 | Eberle et al. |
| 7,713,260 B2 | 5/2010 | Lessard |
| 7,758,572 B2 | 7/2010 | Weber et al. |
| 7,810,395 B2 | 10/2010 | Zhou |
| 7,850,685 B2 | 12/2010 | Kunis et al. |
| 7,867,178 B2 | 1/2011 | Simnacher |
| 7,972,299 B2 | 7/2011 | Carter |
| 7,985,189 B1 | 7/2011 | Ogden et al. |
| 8,162,859 B2 | 4/2012 | Schultheiss et al. |
| 8,166,825 B2 | 5/2012 | Zhou |
| 8,192,368 B2 | 6/2012 | Woodruff |
| 8,292,913 B2 | 10/2012 | Warnack |
| 8,328,820 B2 | 12/2012 | Diamant |
| 8,364,235 B2 | 1/2013 | Kordis et al. |
| 8,419,613 B2 | 4/2013 | Saadat |
| 8,439,890 B2 | 5/2013 | Beyar |
| 8,556,813 B2 | 10/2013 | Cashman et al. |
| 8,574,247 B2 | 11/2013 | Adams et al. |
| 8,657,814 B2 | 2/2014 | Werneth |
| 8,709,075 B2 | 4/2014 | Adams et al. |
| 8,728,091 B2 | 5/2014 | Hakala et al. |
| 8,747,416 B2 | 6/2014 | Hakala et al. |
| 8,888,788 B2 | 11/2014 | Hakala et al. |
| 8,956,371 B2 | 2/2015 | Hawkins et al. |
| 8,956,374 B2 | 2/2015 | Hawkins et al. |
| 8,986,339 B2 | 3/2015 | Warnack |
| 8,992,817 B2 | 3/2015 | Stamberg |
| 9,005,216 B2 | 4/2015 | Hakala et al. |
| 9,011,462 B2 | 4/2015 | Adams et al. |
| 9,011,463 B2 | 4/2015 | Adams et al. |
| 9,044,618 B2 | 6/2015 | Hawkins et al. |
| 9,044,619 B2 | 6/2015 | Hawkins et al. |
| 9,072,534 B2 | 7/2015 | Adams et al. |
| 9,131,949 B2 | 9/2015 | Coleman et al. |
| 9,138,249 B2 | 9/2015 | Adams et al. |
| 9,138,260 B2 | 9/2015 | Miller et al. |
| 9,180,280 B2 | 11/2015 | Hawkins et al. |
| 9,220,521 B2 | 12/2015 | Hawkins et al. |
| 9,237,984 B2 | 1/2016 | Hawkins et al. |
| 9,289,132 B2 | 3/2016 | Ghaffari et al. |
| 9,289,224 B2 | 3/2016 | Adams et al. |
| 9,320,530 B2 | 4/2016 | Grace |
| 9,333,000 B2 | 5/2016 | Hakala et al. |
| 9,375,223 B2 | 6/2016 | Wallace |
| 9,421,025 B2 | 8/2016 | Hawkins et al. |
| 9,433,428 B2 | 9/2016 | Hakala et al. |
| 9,504,809 B2 | 11/2016 | Bo |
| 9,510,887 B2 | 12/2016 | Burnett |
| 9,522,012 B2 | 12/2016 | Adams |
| 9,554,815 B2 | 1/2017 | Adams et al. |
| 9,555,267 B2 | 1/2017 | Ein-gal |
| 9,566,209 B2 | 2/2017 | Katragadda et al. |
| 9,579,114 B2 | 2/2017 | Mantell et al. |
| 9,629,567 B2 | 4/2017 | Porath et al. |
| 9,642,673 B2 | 5/2017 | Adams |
| 9,662,069 B2 | 5/2017 | De Graff et al. |
| 9,687,166 B2 | 6/2017 | Subramaniam |
| 9,730,715 B2 | 8/2017 | Adams |
| 9,764,142 B2 | 9/2017 | Imran |
| 9,814,476 B2 | 11/2017 | Adams et al. |
| 9,861,377 B2 | 1/2018 | Mantell et al. |
| 9,867,629 B2 | 1/2018 | Hawkins et al. |
| 9,894,756 B2 | 2/2018 | Weinkam et al. |
| 9,955,946 B2 | 5/2018 | Miller et al. |
| 9,974,963 B2 | 5/2018 | Imran |
| 9,974,970 B2 | 5/2018 | Nuta et al. |
| 9,993,292 B2 | 6/2018 | Adams et al. |
| 10,039,561 B2 | 8/2018 | Adams et al. |
| 10,136,829 B2 | 11/2018 | Deno et al. |
| 10,149,690 B2 | 12/2018 | Hawkins et al. |
| 10,159,505 B2 | 12/2018 | Hakala et al. |
| 10,194,994 B2 | 2/2019 | Deno et al. |
| 10,201,387 B2 | 2/2019 | Grace et al. |
| 10,206,698 B2 | 2/2019 | Hakala et al. |
| 10,226,265 B2 | 3/2019 | Ku et al. |
| 10,357,264 B2 | 7/2019 | Kat-Kuoy |
| 10,405,923 B2 | 9/2019 | Yu et al. |

(56) References Cited

U.S. PATENT DOCUMENTS

| | | |
|---|---|---|
| 10,406,031 B2 | 9/2019 | Thyzel |
| 10,420,569 B2 | 9/2019 | Adams |
| 10,441,300 B2 | 10/2019 | Hawkins |
| 10,478,202 B2 | 11/2019 | Adams et al. |
| 10,517,620 B2 | 12/2019 | Adams |
| 10,517,621 B1 | 12/2019 | Hakala et al. |
| 10,537,287 B2 | 1/2020 | Braido et al. |
| 10,555,744 B2 | 2/2020 | Nguyen et al. |
| 10,561,428 B2 | 2/2020 | Eggert et al. |
| 10,646,240 B2 | 5/2020 | Betelia et al. |
| 10,682,178 B2 | 6/2020 | Adams et al. |
| 10,702,293 B2 | 7/2020 | Adams et al. |
| 10,709,462 B2 | 7/2020 | Nguyen et al. |
| 10,758,255 B2 | 9/2020 | Adams |
| 10,842,567 B2 | 11/2020 | Grace et al. |
| 10,959,743 B2 | 3/2021 | Adams et al. |
| 10,966,737 B2 | 4/2021 | Nguyen |
| 10,967,156 B2 | 4/2021 | Gulachenski |
| 10,973,538 B2 | 4/2021 | Hakala et al. |
| 11,000,299 B2 | 5/2021 | Hawkins et al. |
| 11,020,135 B1 | 6/2021 | Hawkins |
| 11,026,707 B2 | 6/2021 | Ku et al. |
| 11,058,492 B2 | 7/2021 | Grace et al. |
| 11,076,874 B2 | 8/2021 | Hakala et al. |
| 11,213,661 B2 | 1/2022 | Spindler |
| 11,229,772 B2 | 1/2022 | Nita |
| 11,229,776 B2 | 1/2022 | Kugler et al. |
| 11,246,659 B2 | 2/2022 | Grace et al. |
| 2001/0016761 A1 | 8/2001 | Rudie |
| 2001/0051784 A1 | 12/2001 | Brisken |
| 2002/0045811 A1 | 4/2002 | Kittrell et al. |
| 2002/0065512 A1 | 5/2002 | Fjield et al. |
| 2002/0082553 A1 | 6/2002 | Duchamp |
| 2002/0183729 A1 | 12/2002 | Farr et al. |
| 2002/0188204 A1 | 12/2002 | McNamara et al. |
| 2003/0009157 A1 | 1/2003 | Levine et al. |
| 2003/0050632 A1 | 3/2003 | Fjield et al. |
| 2003/0065316 A1 | 4/2003 | Levine et al. |
| 2003/0114901 A1 | 6/2003 | Loeb et al. |
| 2003/0125719 A1* | 7/2003 | Furnish ............... A61B 1/07 606/15 |
| 2003/0176873 A1 | 9/2003 | Chernenko et al. |
| 2004/0002677 A1 | 1/2004 | Gentsler |
| 2004/0073251 A1 | 4/2004 | Weber |
| 2004/0097996 A1 | 5/2004 | Rabiner |
| 2004/0133254 A1 | 7/2004 | Sterzer et al. |
| 2004/0162508 A1 | 8/2004 | Uebelacker |
| 2004/0243119 A1 | 12/2004 | Lane et al. |
| 2004/0249401 A1 | 12/2004 | Rabiner |
| 2004/0254570 A1 | 12/2004 | Hadsjicostis |
| 2005/0010095 A1 | 1/2005 | Stewart et al. |
| 2005/0021013 A1 | 1/2005 | Visuri |
| 2005/0080396 A1 | 4/2005 | Rontal |
| 2005/0113722 A1 | 5/2005 | Schultheiss |
| 2005/0171437 A1 | 8/2005 | Carberry |
| 2005/0171527 A1 | 8/2005 | Bhola |
| 2005/0251131 A1 | 11/2005 | Lesh |
| 2005/0259319 A1 | 11/2005 | Brooker |
| 2005/0273014 A1 | 12/2005 | Gianchandani et al. |
| 2005/0277839 A1 | 12/2005 | Alderman et al. |
| 2006/0033241 A1 | 2/2006 | Schewe et al. |
| 2006/0084966 A1 | 4/2006 | Maguire et al. |
| 2006/0098921 A1 | 5/2006 | Benaron et al. |
| 2006/0190022 A1 | 8/2006 | Beyar et al. |
| 2006/0200039 A1 | 9/2006 | Brockway et al. |
| 2006/0221528 A1 | 10/2006 | Li et al. |
| 2006/0241524 A1 | 10/2006 | Lee et al. |
| 2006/0241572 A1 | 10/2006 | Zhou |
| 2006/0241733 A1 | 10/2006 | Zhang et al. |
| 2006/0270976 A1 | 11/2006 | Savage et al. |
| 2007/0043340 A1 | 2/2007 | Thyzel |
| 2007/0060990 A1 | 3/2007 | Satake |
| 2007/0088380 A1 | 4/2007 | Hirszowicz et al. |
| 2007/0118057 A1 | 5/2007 | Ein-gal |
| 2007/0142819 A1 | 6/2007 | El-Nounou et al. |
| 2007/0179496 A1 | 8/2007 | Swoyer |
| 2007/0239082 A1 | 10/2007 | Schultheiss et al. |
| 2007/0255270 A1 | 11/2007 | Carney |
| 2007/0264353 A1 | 11/2007 | Myntti et al. |
| 2007/0270897 A1 | 11/2007 | Skerven |
| 2007/0280311 A1 | 12/2007 | Hofmann |
| 2007/0299392 A1 | 12/2007 | Beyar et al. |
| 2008/0086118 A1 | 4/2008 | Lai |
| 2008/0095714 A1 | 4/2008 | Castella et al. |
| 2008/0097251 A1 | 4/2008 | Babaev |
| 2008/0108867 A1 | 5/2008 | Zhou |
| 2008/0114341 A1 | 5/2008 | Thyzel |
| 2008/0132810 A1 | 6/2008 | Scoseria et al. |
| 2008/0195088 A1 | 8/2008 | Farr et al. |
| 2008/0214891 A1 | 9/2008 | Slenker et al. |
| 2008/0296152 A1 | 12/2008 | Voss |
| 2008/0319356 A1 | 12/2008 | Cain et al. |
| 2009/0036803 A1 | 2/2009 | Warlick et al. |
| 2009/0043300 A1 | 2/2009 | Reitmajer et al. |
| 2009/0054881 A1 | 2/2009 | Krespi |
| 2009/0097806 A1 | 4/2009 | Viellerobe et al. |
| 2009/0125007 A1 | 5/2009 | Splinter |
| 2009/0192495 A1 | 7/2009 | Ostrovsky et al. |
| 2009/0247945 A1 | 10/2009 | Levit |
| 2009/0296751 A1 | 12/2009 | Kewitsch et al. |
| 2009/0299327 A1 | 12/2009 | Tilson et al. |
| 2009/0306533 A1 | 12/2009 | Rousche |
| 2009/0312768 A1 | 12/2009 | Hawkins et al. |
| 2010/0016862 A1 | 1/2010 | Hawkins et al. |
| 2010/0036294 A1 | 2/2010 | Mantell et al. |
| 2010/0114020 A1 | 5/2010 | Hawkins et al. |
| 2010/0114065 A1 | 5/2010 | Hawkins et al. |
| 2010/0125268 A1 | 5/2010 | Gustus et al. |
| 2010/0160903 A1 | 6/2010 | Krespi |
| 2010/0168572 A1 | 7/2010 | Sliwa |
| 2010/0179632 A1 | 7/2010 | Bruszewski et al. |
| 2010/0191089 A1 | 7/2010 | Stebler et al. |
| 2010/0198114 A1 | 8/2010 | Novak et al. |
| 2010/0199773 A1 | 8/2010 | Zhou |
| 2010/0222786 A1 | 9/2010 | Kassab |
| 2010/0234875 A1 | 9/2010 | Allex et al. |
| 2010/0256535 A1 | 10/2010 | Novak et al. |
| 2011/0034832 A1 | 2/2011 | Cioanta et al. |
| 2011/0059415 A1 | 3/2011 | Kasenbacher |
| 2011/0082452 A1 | 4/2011 | Melsky |
| 2011/0082534 A1 | 4/2011 | Wallace |
| 2011/0118634 A1 | 5/2011 | Golan |
| 2011/0144502 A1 | 6/2011 | Zhou et al. |
| 2011/0184244 A1 | 7/2011 | Kagaya et al. |
| 2011/0208185 A1 | 8/2011 | Diamant et al. |
| 2011/0213349 A1 | 9/2011 | Brown |
| 2011/0245740 A1 | 10/2011 | Novak et al. |
| 2011/0257641 A1 | 10/2011 | Hastings et al. |
| 2011/0263921 A1 | 10/2011 | Vrba et al. |
| 2011/0275990 A1 | 11/2011 | Besser et al. |
| 2012/0064141 A1 | 3/2012 | Andreacchi et al. |
| 2012/0071715 A1 | 3/2012 | Beyar et al. |
| 2012/0071867 A1 | 3/2012 | Ryan |
| 2012/0071889 A1 | 3/2012 | Mantell et al. |
| 2012/0095335 A1 | 4/2012 | Sverdlik et al. |
| 2012/0095461 A1 | 4/2012 | Herscher et al. |
| 2012/0116289 A1 | 5/2012 | Hawkins et al. |
| 2012/0116486 A1 | 5/2012 | Naga et al. |
| 2012/0123331 A1 | 5/2012 | Satake |
| 2012/0123399 A1 | 5/2012 | Belikov |
| 2012/0157892 A1 | 6/2012 | Reitmajer et al. |
| 2012/0203255 A1 | 8/2012 | Hawkins et al. |
| 2012/0221013 A1 | 8/2012 | Hawkins et al. |
| 2012/0232409 A1 | 9/2012 | Stahmann |
| 2012/0296367 A1 | 11/2012 | Grovender et al. |
| 2012/0330293 A1 | 12/2012 | Arai |
| 2013/0030431 A1 | 1/2013 | Adams |
| 2013/0030447 A1 | 1/2013 | Adams |
| 2013/0041355 A1 | 2/2013 | Heeren et al. |
| 2013/0046207 A1 | 2/2013 | Capelli |
| 2013/0046293 A1 | 2/2013 | Arai et al. |
| 2013/0053762 A1 | 2/2013 | Rontal et al. |
| 2013/0116714 A1 | 5/2013 | Adams et al. |
| 2013/0190803 A1 | 7/2013 | Angel et al. |

(56) References Cited

U.S. PATENT DOCUMENTS

| | | |
|---|---|---|
| 2013/0197614 A1 | 8/2013 | Gustus |
| 2013/0218054 A1 | 8/2013 | Sverdlik et al. |
| 2013/0226131 A1 | 8/2013 | Bacino et al. |
| 2013/0253466 A1 | 9/2013 | Campbell |
| 2013/0345617 A1 | 12/2013 | Wallace |
| 2014/0005576 A1 | 1/2014 | Adams |
| 2014/0005706 A1 | 1/2014 | Gelfand et al. |
| 2014/0012186 A1 | 1/2014 | Thyzel |
| 2014/0039002 A1 | 1/2014 | Adams et al. |
| 2014/0039358 A1 | 2/2014 | Zhou et al. |
| 2014/0039513 A1 | 2/2014 | Hakala |
| 2014/0046229 A1 | 2/2014 | Hawkins et al. |
| 2014/0046353 A1 | 2/2014 | Adams |
| 2014/0052146 A1 | 2/2014 | Curtis et al. |
| 2014/0052147 A1 | 2/2014 | Hakala et al. |
| 2014/0058294 A1 | 2/2014 | Gross et al. |
| 2014/0074111 A1 | 3/2014 | Hakala |
| 2014/0153087 A1 | 6/2014 | Hutchings et al. |
| 2014/0155990 A1 | 6/2014 | Nyuli |
| 2014/0180069 A1 | 6/2014 | Millett |
| 2014/0180126 A1 | 6/2014 | Millett |
| 2014/0180134 A1 | 6/2014 | Hoseit |
| 2014/0188094 A1 | 7/2014 | Islam |
| 2014/0228829 A1 | 8/2014 | Schmitt |
| 2014/0257144 A1 | 9/2014 | Capelli et al. |
| 2014/0257148 A1 | 9/2014 | Jie |
| 2014/0276573 A1 | 9/2014 | Miesel |
| 2014/0288570 A1 | 9/2014 | Adams |
| 2014/0357997 A1 | 12/2014 | Hartmann |
| 2015/0005576 A1 | 1/2015 | Diodone et al. |
| 2015/0039002 A1 | 2/2015 | Hawkins |
| 2015/0073430 A1 | 3/2015 | Hakala et al. |
| 2015/0080875 A1 | 3/2015 | Kasprzyk et al. |
| 2015/0100048 A1 | 4/2015 | Hiereth et al. |
| 2015/0105715 A1 | 4/2015 | Pikus et al. |
| 2015/0119870 A1 | 4/2015 | Rudie |
| 2015/0141764 A1 | 5/2015 | Harks et al. |
| 2015/0250542 A1 | 9/2015 | Islam |
| 2015/0276689 A1 | 10/2015 | Watanabe et al. |
| 2015/0313732 A1 | 11/2015 | Fulton, III |
| 2015/0359432 A1 | 12/2015 | Ehrenreich |
| 2016/0008016 A1 | 1/2016 | Cioanta et al. |
| 2016/0016016 A1 | 1/2016 | Taylor et al. |
| 2016/0018602 A1 | 1/2016 | Govari et al. |
| 2016/0022294 A1 | 1/2016 | Cioanta et al. |
| 2016/0038087 A1 | 2/2016 | Hunter |
| 2016/0095610 A1 | 4/2016 | Lipowski et al. |
| 2016/0135828 A1 | 5/2016 | Hawkins et al. |
| 2016/0143522 A1 | 5/2016 | Ransbury |
| 2016/0151639 A1 | 6/2016 | Scharf et al. |
| 2016/0183819 A1 | 6/2016 | Burnett |
| 2016/0183957 A1 | 6/2016 | Hakala et al. |
| 2016/0184020 A1 | 6/2016 | Kowalewski et al. |
| 2016/0184022 A1 | 6/2016 | Grace et al. |
| 2016/0184023 A1 | 6/2016 | Grace et al. |
| 2016/0184570 A1 | 6/2016 | Grace et al. |
| 2016/0262784 A1 | 9/2016 | Grace et al. |
| 2016/0270806 A1 | 9/2016 | Wallace |
| 2016/0234534 A1 | 11/2016 | Hawkins et al. |
| 2016/0324564 A1 | 11/2016 | Gerlach et al. |
| 2016/0331389 A1 | 11/2016 | Hakala et al. |
| 2016/0367274 A1 | 12/2016 | Wallace |
| 2016/0367275 A1 | 12/2016 | Wallace |
| 2017/0049463 A1 | 2/2017 | Popovic et al. |
| 2017/0056035 A1 | 3/2017 | Adams |
| 2017/0086867 A1 | 3/2017 | Adams |
| 2017/0119469 A1 | 5/2017 | Shimizu et al. |
| 2017/0119470 A1 | 5/2017 | Diamant et al. |
| 2017/0135709 A1 | 5/2017 | Nguyen et al. |
| 2017/0151421 A1 | 6/2017 | Asher |
| 2017/0209050 A1 | 7/2017 | Fengler et al. |
| 2017/0265942 A1 | 9/2017 | Grace et al. |
| 2017/0303946 A1 | 10/2017 | Ku et al. |
| 2017/0311965 A1 | 11/2017 | Adams |
| 2018/0008348 A1 | 1/2018 | Grace et al. |
| 2018/0042661 A1 | 2/2018 | Long |
| 2018/0042677 A1 | 2/2018 | Yu et al. |
| 2018/0049877 A1 | 2/2018 | Venkatasubramanian |
| 2018/0085174 A1 | 3/2018 | Radtke et al. |
| 2018/0092763 A1 | 4/2018 | Dagan et al. |
| 2018/0095287 A1 | 4/2018 | Jeng et al. |
| 2018/0098779 A1 | 4/2018 | Betelia et al. |
| 2018/0152568 A1 | 6/2018 | Kat-kuoy |
| 2018/0238675 A1 | 8/2018 | Wan |
| 2018/0256250 A1 | 9/2018 | Adams et al. |
| 2018/0280005 A1 | 10/2018 | Parmentier |
| 2018/0303501 A1 | 10/2018 | Hawkins |
| 2018/0303503 A1 | 10/2018 | Eggert et al. |
| 2018/0303504 A1 | 10/2018 | Eggert et al. |
| 2018/0304053 A1 | 10/2018 | Eggert et al. |
| 2018/0333043 A1 | 11/2018 | Teriluc |
| 2018/0360482 A1 | 12/2018 | Nguyen |
| 2019/0029702 A1 | 1/2019 | De Cicco |
| 2019/0029703 A1 | 1/2019 | Wasdyke et al. |
| 2019/0069916 A1 | 3/2019 | Hawkins et al. |
| 2019/0097380 A1 | 3/2019 | Luft et al. |
| 2019/0099588 A1 | 4/2019 | Ramanath et al. |
| 2019/0104933 A1 | 4/2019 | Stern |
| 2019/0117242 A1 | 4/2019 | Lawinger |
| 2019/0150960 A1 | 5/2019 | Nguyen et al. |
| 2019/0175111 A1 | 6/2019 | Genereux et al. |
| 2019/0175300 A1 | 6/2019 | Horn et al. |
| 2019/0175372 A1 | 6/2019 | Boyden et al. |
| 2019/0175407 A1 | 6/2019 | Bacher |
| 2019/0209368 A1 | 7/2019 | Park et al. |
| 2019/0232066 A1 | 8/2019 | Lim et al. |
| 2019/0247680 A1 | 8/2019 | Mayer |
| 2019/0262594 A1 | 8/2019 | Ogata et al. |
| 2019/0265419 A1 | 8/2019 | Tayebati |
| 2019/0282249 A1 | 9/2019 | Tran et al. |
| 2019/0282250 A1 | 9/2019 | Tran et al. |
| 2019/0328259 A1 | 10/2019 | Deno et al. |
| 2019/0365400 A1 | 12/2019 | Adams et al. |
| 2019/0388002 A1 | 12/2019 | Bozsak et al. |
| 2019/0388110 A1 | 12/2019 | Nguyen et al. |
| 2019/0388133 A1 | 12/2019 | Sharma |
| 2019/0388151 A1 | 12/2019 | Bhawalkar |
| 2020/0000484 A1 | 1/2020 | Hawkins |
| 2020/0008856 A1 | 1/2020 | Harmouche |
| 2020/0022754 A1 | 1/2020 | Cottone |
| 2020/0038087 A1 | 2/2020 | Harmouche |
| 2020/0046949 A1 | 2/2020 | Chisena et al. |
| 2020/0054352 A1 | 2/2020 | Brouillette et al. |
| 2020/0061931 A1 | 2/2020 | Brown et al. |
| 2020/0069371 A1 | 3/2020 | Brown et al. |
| 2020/0085458 A1 | 3/2020 | Nguyen et al. |
| 2020/0085459 A1 | 3/2020 | Adams |
| 2020/0107960 A1 | 4/2020 | Bacher |
| 2020/0108236 A1 | 4/2020 | Salazar et al. |
| 2020/0129195 A1 | 4/2020 | McGowan et al. |
| 2020/0129741 A1 | 4/2020 | Kawwas |
| 2020/0155812 A1 | 5/2020 | Zhang et al. |
| 2020/0197019 A1 | 6/2020 | Harper |
| 2020/0205890 A1 | 7/2020 | Harlev |
| 2020/0246032 A1 | 8/2020 | Betelia et al. |
| 2020/0289202 A1 | 9/2020 | Miyagawa et al. |
| 2020/0297366 A1 | 9/2020 | Nguyen et al. |
| 2020/0337717 A1 | 10/2020 | Walzman |
| 2020/0383724 A1 | 12/2020 | Adams et al. |
| 2020/0397230 A1* | 12/2020 | Massimini ............ A61B 5/027 |
| 2020/0397453 A1 | 12/2020 | McGowan et al. |
| 2020/0398033 A1 | 12/2020 | McGowan et al. |
| 2020/0405333 A1 | 12/2020 | Massimini et al. |
| 2020/0405391 A1 | 12/2020 | Massimini et al. |
| 2020/0406009 A1 | 12/2020 | Massimini et al. |
| 2020/0406010 A1 | 12/2020 | Massimini et al. |
| 2021/0038237 A1 | 2/2021 | Adams |
| 2021/0085347 A1 | 3/2021 | Phan et al. |
| 2021/0085348 A1 | 3/2021 | Nguyen |
| 2021/0085383 A1 | 3/2021 | Vo et al. |
| 2021/0128241 A1 | 5/2021 | Schultheis |
| 2021/0137598 A1 | 5/2021 | Cook |
| 2021/0153939 A1* | 5/2021 | Cook .................... A61B 18/26 |
| 2021/0177445 A1 | 6/2021 | Nguyen |

(56) References Cited

U.S. PATENT DOCUMENTS

| | | |
|---|---|---|
| 2021/0186613 A1 | 6/2021 | Cook |
| 2021/0212765 A1 | 7/2021 | Verhagen |
| 2021/0220052 A1 | 7/2021 | Cook |
| 2021/0220053 A1 | 7/2021 | Cook |
| 2021/0244473 A1 | 8/2021 | Cook et al. |
| 2021/0267685 A1 | 9/2021 | Schultheis |
| 2021/0275247 A1 | 9/2021 | Schultheis |
| 2021/0275249 A1 | 9/2021 | Massimini et al. |
| 2021/0282792 A1 | 9/2021 | Adams et al. |
| 2021/0290259 A1 | 9/2021 | Hakala et al. |
| 2021/0290286 A1 | 9/2021 | Cook |
| 2021/0290305 A1 | 9/2021 | Cook |
| 2021/0298603 A1 | 9/2021 | Feldman |
| 2021/0338258 A1 | 11/2021 | Hawkins et al. |
| 2021/0353359 A1 | 11/2021 | Cook |
| 2021/0369348 A1 | 12/2021 | Cook |
| 2021/0378743 A1 | 12/2021 | Massimini et al. |
| 2021/0386479 A1 | 12/2021 | Massimini et al. |
| 2022/0000505 A1 | 1/2022 | Hauser |
| 2022/0000506 A1 | 1/2022 | Hauser |
| 2022/0000507 A1 | 1/2022 | Hauser |
| 2022/0000508 A1 | 1/2022 | Schmitt et al. |
| 2022/0000509 A1 | 1/2022 | Laser et al. |
| 2022/0000551 A1 | 1/2022 | Govari et al. |
| 2022/0008130 A1 | 1/2022 | Massimini et al. |
| 2022/0008693 A1 | 1/2022 | Humbert et al. |
| 2022/0015785 A1 | 1/2022 | Hakala et al. |
| 2022/0021190 A1 | 1/2022 | Pecquois |
| 2022/0022902 A1 | 1/2022 | Spano |
| 2022/0022912 A1 | 1/2022 | Efremkin |
| 2022/0023528 A1 | 1/2022 | Long et al. |
| 2022/0071704 A1 | 3/2022 | Le |
| 2022/0168594 A1 | 6/2022 | Mayer |
| 2022/0183738 A1 | 6/2022 | Flores et al. |
| 2022/0218402 A1 | 7/2022 | Schultheis |
| 2022/0249165 A1 | 8/2022 | Cook |
| 2022/0273324 A1 | 9/2022 | Schultheis |
| 2022/0354578 A1 | 11/2022 | Cook |
| 2022/0387106 A1 | 12/2022 | Cook |
| 2023/0013920 A1 | 1/2023 | Massimini |

FOREIGN PATENT DOCUMENTS

| | | |
|---|---|---|
| CA | 2229806 | 3/1997 |
| CA | 2983655 | 10/2016 |
| CN | 102057422 | 5/2011 |
| CN | 109223100 | 1/2019 |
| CN | 110638501 A | 1/2020 |
| CN | 106794043 | 3/2020 |
| CN | 107411805 | 1/2022 |
| CN | 107899126 | 1/2022 |
| CN | 109475378 | 1/2022 |
| CN | 113876388 | 1/2022 |
| CN | 113877044 | 1/2022 |
| CN | 113907838 | 1/2022 |
| CN | 113951972 A | 1/2022 |
| CN | 113951973 A | 1/2022 |
| CN | 113974765 | 1/2022 |
| CN | 113974826 A | 1/2022 |
| CN | 113993463 | 1/2022 |
| CN | 215384399 | 1/2022 |
| CN | 215386905 | 1/2022 |
| CN | 215458400 | 1/2022 |
| CN | 215458401 | 1/2022 |
| CN | 215505065 | 1/2022 |
| CN | 215534803 | 1/2022 |
| CN | 215537694 | 1/2022 |
| CN | 215584286 | 1/2022 |
| CN | 215606068 | 1/2022 |
| CN | 215651393 | 1/2022 |
| CN | 215651394 | 1/2022 |
| CN | 215651484 | 1/2022 |
| CN | 215653328 | 1/2022 |
| DE | 3038445 A1 | 5/1982 |
| DE | 3836337 A1 | 4/1990 |
| DE | 3913027 A1 | 10/1990 |
| DE | 202008016760 | 3/2009 |
| DE | 102007046902 | 4/2009 |
| DE | 102008034702 | 1/2010 |
| DE | 102009007129 | 8/2010 |
| DE | 202010009899 | 11/2010 |
| DE | 102013201928 | 8/2014 |
| DE | 102020117713 | 1/2022 |
| EP | 0119296 | 9/1984 |
| EP | 0261831 B1 | 6/1992 |
| EP | 558297 A2 | 9/1993 |
| EP | 0571306 A1 | 11/1993 |
| EP | 1179993 A1 | 2/2002 |
| EP | 1946712 | 7/2008 |
| EP | 1946712 A1 | 7/2008 |
| EP | 2157569 | 2/2010 |
| EP | 2879595 | 6/2015 |
| EP | 2879595 A1 | 6/2015 |
| EP | 2944264 A1 | 6/2015 |
| EP | 3226795 A1 | 10/2017 |
| EP | 3318204 | 5/2018 |
| EP | 3461438 A1 | 4/2019 |
| EP | 3473195 A1 | 4/2019 |
| EP | 3643260 A1 | 4/2020 |
| EP | 3076881 B1 | 1/2022 |
| EP | 3932342 | 1/2022 |
| EP | 3936140 | 1/2022 |
| EP | 4051154 | 9/2022 |
| GB | 1082397 | 9/1967 |
| JP | S62275446 A | 11/1987 |
| KR | 20050098932 | 10/2005 |
| KR | 20080040111 | 5/2008 |
| KR | 20160090877 A | 8/2016 |
| WO | WO9007904 A1 | 7/1990 |
| WO | WO9105332 A1 | 4/1991 |
| WO | 9203095 A1 | 3/1992 |
| WO | WO9208515 | 5/1992 |
| WO | 1999002095 A1 | 1/1999 |
| WO | 1999020189 A1 | 4/1999 |
| WO | WO200067648 | 11/2000 |
| WO | WO2000067648 A1 | 11/2000 |
| WO | WO0103599 A2 | 1/2001 |
| WO | 20060006169 A2 | 1/2006 |
| WO | WO2006006169 | 1/2006 |
| WO | WO2009121017 | 10/2009 |
| WO | WO2009149321 A1 | 12/2009 |
| WO | WO2009152352 A2 | 12/2009 |
| WO | 2010042653 A1 | 4/2010 |
| WO | WO2011094379 | 8/2011 |
| WO | 20110126580 A2 | 10/2011 |
| WO | WO2011126580 A3 | 10/2011 |
| WO | WO2012025833 | 3/2012 |
| WO | WO20120052924 A1 | 4/2012 |
| WO | WO20120120495 A2 | 9/2012 |
| WO | WO2013119662 | 8/2013 |
| WO | 20130169807 A1 | 11/2013 |
| WO | WO2013169807 | 11/2013 |
| WO | WO2014025397 A1 | 2/2014 |
| WO | WO20140022867 A1 | 2/2014 |
| WO | WO2014138582 | 9/2014 |
| WO | WO2015056662 | 4/2015 |
| WO | WO2015097251 A2 | 7/2015 |
| WO | 20150177790 A1 | 11/2015 |
| WO | WO2016089683 A1 | 6/2016 |
| WO | WO2016090175 | 6/2016 |
| WO | WO2016109739 | 7/2016 |
| WO | WO2016151595 A1 | 9/2016 |
| WO | WO20170192869 A1 | 11/2017 |
| WO | 20180022641 A1 | 2/2018 |
| WO | WO2018022593 A1 | 2/2018 |
| WO | WO2018083666 | 5/2018 |
| WO | 20180175322 A1 | 9/2018 |
| WO | WO2018175322 | 9/2018 |
| WO | WO2018191013 | 10/2018 |
| WO | WO2019200201 A1 | 10/2019 |
| WO | WO2019222843 | 11/2019 |
| WO | WO2020056031 | 3/2020 |
| WO | WO20200086361 A1 | 4/2020 |
| WO | WO2020089876 A1 | 5/2020 |

(56) References Cited

FOREIGN PATENT DOCUMENTS

| WO | WO2020157648 |    | 8/2020  |
|----|--------------|----|---------|
| WO | WO2020256898 |    | 12/2020 |
| WO | WO2020256898 | A1 | 12/2020 |
| WO | WO2020256949 |    | 12/2020 |
| WO | WO2020256949 | A1 | 12/2020 |
| WO | WO2020263469 | A1 | 12/2020 |
| WO | WO2020263685 | A1 | 12/2020 |
| WO | WO2020263687 | A1 | 12/2020 |
| WO | WO2020263688 | A1 | 12/2020 |
| WO | WO2020263689 | A1 | 12/2020 |
| WO | WO2021061451 |    | 4/2021  |
| WO | WO2021067563 |    | 4/2021  |
| WO | WO2021086571 | A1 | 5/2021  |
| WO | WO2021096922 | A1 | 5/2021  |
| WO | WO2021101766 |    | 5/2021  |
| WO | WO2021101766 | A1 | 5/2021  |
| WO | WO2021126762 | A1 | 6/2021  |
| WO | WO2021150502 | A1 | 7/2021  |
| WO | WO2021162855 | A1 | 8/2021  |
| WO | WO2021173417 | A1 | 9/2021  |
| WO | WO2021183367 | A1 | 9/2021  |
| WO | WO2021183401 | A1 | 9/2021  |
| WO | WO2021188233 | A1 | 9/2021  |
| WO | WO2021231178 | A1 | 11/2021 |
| WO | WO2021247685 | A1 | 12/2021 |
| WO | WO2021257425 | A1 | 12/2021 |
| WO | WO2022007490 |    | 1/2022  |
| WO | WO2022008440 |    | 1/2022  |
| WO | WO2022010767 | A1 | 1/2022  |
| WO | WO2022055784 |    | 3/2022  |
| WO | WO2022125525 |    | 6/2022  |
| WO | WO2022154954 |    | 7/2022  |
| WO | WO2022173719 |    | 8/2022  |
| WO | WO2022187058 |    | 9/2022  |
| WO | WO2022216488 |    | 10/2022 |
| WO | WO2022240674 |    | 11/2022 |
| WO | WO2022260932 |    | 12/2022 |

OTHER PUBLICATIONS

International Search Report and Written Opinion dated Sep. 14, 2020 in PCT Application Serial No. PCT/US2020/038523.

International Search Report and Written Opinion dated Oct. 2, 2020 in PCT Application Serial No. PCT/US2020/036107.

Schafter+Kirchhoff, Laser Beam Couplers series 60SMS for coupling into single-mode and polarization-maintaining fiber cables, Schafter+Kirchhoff, pp. 1-5, Germany. Dec. 2, 2021.

International Search Report and Written Opinion dated Jan. 29, 2020 in PCT Application Serial No. PCT/US2020/059961.

International Search Report and Written Opinion dated Jan. 20, 2020 in PCT Application Serial No. PCT/US2020/054792.

Partial Search Report and Provisional Opinion dated Feb. 19, 2021 in PCT Application Serial No. PCT/US2020/059960.

Shariat, Mohammad H., et al. "Localization of the ectopic spiral electrical source using intracardiac electrograms during atrial fibrillation." 2015 IEEE 28th Canadian Conference on Electrical and Computer Engineering (CCECE). IEEE, 2015.

Nademanee, Koonlawee, et al. "A new approach for catheter ablation of atrial fibrillation: mapping of the electrophysiologic substrate." Journal of the American College of Cardiology 43.11 (2004): 2044-2053.

Calkins, Hugh. "Three dimensional mapping of atrial fibrillation: techniques and necessity." Journal of interventional cardiac electrophysiology 13.1 (2005): 53-59.

Shariat, Mohammad Hassan. Processing the intracardiac electrogram for atrial fibrillation ablation. Diss. Queen's University (Canada), 2016.

Meng et al., "Accurate Recovery of Atrial Endocardial Potential Maps From Non-contact Electrode Data." Auckland Bioengineering Institute. (ID 1421). May 2019.

Jiang et al., "Multielectrode Catheter for Substrate Mapping for Scar-related VT Ablation: A Comparison Between Grid Versus Linear Configurations." UChicago Medicine, Center for Arrhythmia Care, Chicago IL (ID 1368). Poster for conference in San Francisco, May 8-11, 2019.

Sacher et al., "Comparison of Manual Vs Automatic Annotation to Identify Abnormal Substrate for Scar Related VT Ablation." LIRYC Institute, Bordeaux University Hospital, France (ID 1336). Poster for conference in San Francisco, May 8-11, 2019.

Oriel Instruments, "Introduction to Beam Splitters for Optical Research Applications", Apr. 2014, pp. 1-9, https://www.azoptics.com/Article.aspx?ArticaID=871.

International Search Report and Written Opinion dated Apr. 12, 2021 in PCT Application Serial No. PCT/US2020/059960.

International Search Report and Written Opinion dated Apr. 13, 2021 in PCT Application Serial No. PCT/US2020/064846.

International Search Report and Written Opinion dated Apr. 13, 2021 in PCT Application Serial No. PCT/US2021/013944.

International Search Report and Written Opinion dated May 25, 2021 in PCT Application Serial No. PCT/US2021/017604.

International Search Report and Written Opinion dated Jun. 2, 2021 in PCT Application Serial No. PCT/US2021/018522.

International Search Report and Written Opinion dated Jun. 2, 2021 in PCT Application Serial No. PCT/US2021/015204.

International Search Report and Written Opinion dated Jun. 17, 2021 in PCT Application Serial No. PCT/US2021/020934.

International Search Report and Written Opinion dated Jul. 13, 2021 in PCT Application Serial No. PCT/US2021/024216.

International Search Report and Written Opinion dated Jun. 22, 2021 in PCT Application Serial No. PCT/US2021/020937.

International Search Report and Written Opinion dated Jun. 24, 2021 in PCT Application Serial No. PCT/US2021/021272.

International Search Report and Written Opinion dated Aug. 20, 2021 in PCT Application Serial No. PCT/US2021/031130.

International Search Report and Written Opinion dated Apr. 4, 2022 in PCT Application Serial No. PCT/US2021/062170.

International Search Report and Written Opinion dated Apr. 4, 2022 in PCT Application Serial No. PCT/US2021/065073.

Partial Search Report and Provisional Opinion dated May 3, 2022 in PCT Application No. PCT/US2022/015577.

International Search Report and Written Opinion dated May 13, 2022 in PCT Application Serial No. PCT/US2022/017562.

International Search Report and Written Opinion dated Jun. 28, 2022, in PCT Application Serial No. PCT/US2022/015577.

International Search Report and Written Opinion dated Jun. 27, 2022, in PCT Application Serial No. PCT/US2022/022460.

International Search Report and Written Opinion dated Aug. 25, 2022 in PCT Application Serial No. PCT US/2022/028035.

International Search Report and Written Opinion dated Sep. 15, 2022 in PCT Application Serial No. PCT US/2022/032045.

International Search Report and Written Opinion dated Nov. 8, 2022 in PCT Application Serial No. PCT US/2022/039678.

Davletshin, Yevgeniy R., "A Computational Analysis of Nanoparticle-Mediated Optical Breakdown", A dissertation presented to Ryerson University in Partial Fulfillment of the requirements for the degree of Doctor of Philosophy in the Program of Physics, Toronto, Ontario, CA 2017.

Vogel, A., et al. "Acoustic transient generation by laser-produced cavitation bubbles near solid boundaries", Journal Acoustical Society of America, 1988, pp. 719-731, vol. 84.

Asshauer, T., et al. "Acoustic transient generation by holmium-laser-induced cavitation bubbles", Journal of Applied Physics, Nov. 1, 1994, pp. 5007-5013, vol. 76, No. 9, American Institute of Physics.

Zheng, W., "Optic Lenses Manufactured on Fiber Ends", 2015, Splicer Engineering AFL, Duncan, SC USA.

Ali, Ziad A., et al. "Optical Coherence Tomography Characterization of Coronary Lithoplasty for Treatment of Calcified Lesions", JACC: Cardiovascular Imaging, 2017, pp. 897-906, vol. 109, No. 8, Elsevier.

Ali, Ziad A., et al. "Intravascular lithotripsy for treatment of stent underexpansion secondary to severe coronary calcification" 2018, European Society of Cardiology.

(56) References Cited

OTHER PUBLICATIONS

Ashok, Praveen C., et al. "Raman spectroscopy bio-sensor for tissue discrimination in surgical robotics—full article", Journal of Biophotonics, 2014, pp. 103-109, vol. 7, No. 1-2.

Ashok, Praveen C., et al. "Raman spectroscopy bio-sensor for tissue discrimination in surgical robotics—proof" Journal of Biophotonics 7, 2014, No. 1-2.

Bian, D. C., et al. "Experimental Study of Pulsed Discharge Underwater Shock-Related Properties in Pressurized Liquid Water", Hindawi Advances in Materials Science and Engineering, Jan. 2018, 12 pages, vol. 2018, Article ID 8025708.

Bian, D. C., et al. "Study on Breakdown Delay Characteristics Based on High-voltage Pulse Discharge in Water with Hydrostatic Pressure", Journal of Power Technologies 97(2), 2017, pp. 89-102.

Doukas, A. G., et al. "Biological effects of laser induced shock waves: Structural and functional cell damage in vitro", Ultrasound in Medicine and Biology, 1993, pp. 137-146, vol. 19, Issue 2, Pergamon Press, USA.

Brodmann, Marianne et al. "Safety and Performance of Lithoplasty for Treatment of Calcified Peripheral Artery Lesions", JACC, 2017, vol. 70, No. 7.

Brouillette, M., "Shock Waves at Microscales", 2003, pp. 3-12, Springer-Verlag.

Mirshekari, G., et al. "Shock Waves in Microchannels", 2013, pp. 259-283, vol. 724, Cambridge University Press.

"Bubble Dynamics and Shock Waves", Springer, 2013, Springer-Verlag, Berlin Heildelberg.

Hardy, Luke A., et al. "Cavitation Bubble Dynamics During Thulium Fiber Laser Lithotripsy", SPIE, Feb. 29, 2016, vol. 9689, San Francisco, California, USA.

Claverie, A., et al. "Experimental characterization of plasma formation and shockwave propagation induced by high power pulsed underwater electrical discharge", Review of Scientific Instruments, 2014, American Institute of Physics.

Blackmon, Richard L., et al. "Comparison of holmium: YAG and thulium fiber laser lithotripsy ablation thresholds, ablation rates, and retropulsion effects", Journal of Biomedical Optics, 2011, vol. 16(7), SPIE.

Debasis, P., et al. "Continuous-wave and quasi-continuous wave thulium-doped all-fiber laser: implementation on kidney stone fragmentations", Applied Optics, Aug. 10, 2016, vol. 55, No. 23, Optical Society of America.

Cook, Jason R., et al. "Tissue mimicking phantoms for photoacoustic and ultrasonic imaging", Biomedical Optics Express, 2011, vol. 2, No. 11, Optical Society of America.

Deckelbaum, Lawrence I., "Coronary Laser Angioplasty", Lasers in Surgery and Medicine, 1994, pp. 101-110, Wiley-Liss Inc.

Costanzo, F., "Underwater Explosion Phenomena and Shock Physics", Research Gate, 2011.

Mizeret, J. C., et al. "Cylindrical fiber optic light diffuser for medical applications", Lasers in Surgery and Medicine, 1996, pp. 159-167, vol. 19, Issue 2, Wiley-Liss Inc., Lausanne, Switzerland.

De Silva, K., et al. "A Calcific, Undilatable Stenosis Lithoplasty, a New Tool in the Box?", JACC: Cardiovascular Interventions, 2017, vol. 10, No. 3, Elsevier.

Vesselov, L., et al. "Design and performance of thin cylindrical diffusers created in Ge-doped multimode optical fibers", Applied Optics, 2005, pp. 2754-2758, vol. 44, Issue 14, Optical Society of America.

Hutchens, Thomas C., et al. "Detachable fiber optic tips for use in thulium fiber laser lithotripsy", Journal of Biomedical Optics, Mar. 2013, vol. 18(3), SPIE.

Kostanski, Kris L., et al. "Development of Novel Tunable Light Scattering Coating Materials for Fiber Optic Diffusers in Photodynamic Cancer Therapy", Journal of Applied Polymer Science, 2009, pp. 1516-1523, vol. 112, Wiley InterScience.

Kristiansen, M., et al. "High Voltage Water Breakdown Studies", DoD, 1998, Alexandria, VA, USA.

Dwyer, J. R., et al. "A study of X-ray emission from laboratory sparks in air at atmospheric pressure", Journal of Geophysical Research, 2008, vol. 113, American Geophysical Union.

Jansen, Duco E., et al. "Effect of Pulse Duration on Bubble Formation and Laser-Induced Pressure Waves During Holmium Laser Ablation", Lasers in Surgery and Medicine 18, 1996, pp. 278-293, Wiley-Liss Inc., Austin, TX, USA.

Shangguan, HanQun et al. "Effects of Material Properties on Laser-induced Bubble Formation in Absorbing Liquids and on Submerged Targets", SPIE, 1997, pp. 783-791, vol. 2869.

Varghese, B., et al. "Effects of polarization and absorption on laser induced optical breakdown threshold for skin rejuvenation", SPIE, Mar. 9, 2016, vol. 9740, SPIE, San Francisco, USA.

Varghese, B., et al. "Effects of polarization and apodization on laser induced optical breakdown threshold", Optics Express, Jul. 29, 2013, vol. 21, No. 15, Optical Society of America.

Bonito, Valentina, "Effects of polarization, plasma and thermal initiation pathway on irradiance threshold of laser Induced optical breakdown", Philips Research, 2013, The Netherlands.

Vogel, A. et al. "Energy balance of optical breakdown in water at nanosecond to femtosecond time scales", Applied Physics B 68, 1999, pp. 271-280, Springer-Verlag.

Kang, Hyun W., et al. "Enhanced photocoagulation with catheter based diffusing optical device", Journal of Biomedical Optics, Nov. 2012, vol. 17(11), SPIE.

Esch, E., et al. "A Simple Method for Fabricating Artificial Kidney Stones of Different Physical Properties", National Institute of Health Public Access Author Manuscript, Aug. 2010.

Isner, Jeffrey M., et al. "Excimer Laser Atherectomy", Circulation, Jun. 1990, vol. 81, No. 6, American Heart Association, Dallas, TX, USA.

Israel, Douglas H., et al. "Excimer Laser-Facilitated Balloon Angioplasty of a Nondilateable Lesion", JACC, Oct. 1991, vol. 18, No. 4, American College of Cardiology, New York, USA.

Van Leeuwen, Ton G., et al. "Excimer Laser Induced Bubble: Dimensions, Theory, and Implications for Laser Angioplasty", Lasers in Surgery and Medicine 18, 1996, pp. 381-390, Wiley-Liss Inc., Utrecht, The Netherlands.

Nguyen, H., et al. "Fabrication of multipoint side-firing optical fiber by laser micro-ablation", Optics Letters, May 1, 2017, vol. 42, No. 9, Optical Society of America.

Zheng, W., "Optic Lenses Manufactured on Fiber Ends", 2015, IEEE, Duncan, SC, USA.

Whitesides, George M., et al. "Fluidic Optics", 2006, vol. 6329, SPIE, Cambridge, MA, USA.

Forero, M., et al. "Coronary lithoplasty: a novel treatment for stent underexpansion", Cardiovascular Flashlight, 2018, European Society of Cardiology.

Ghanate, A. D., et al. "Comparative evaluation of spectroscopic models using different multivariate statistical tools in a multicancer scenario", Journal of Biomedical Optics, Feb. 2011, pp. 1-9, vol. 16(2), SPIE.

Roberts, Randy M., et al. "The Energy Partition of Underwater Sparks", The Journal of the Acoustical Society of America, Jun. 1996, pp. 3465-3474, Acoustical Society of America, Austin, TX, USA.

Blackmon, Richard L., et al. "Holmium: YAG Versus Thulium Fiber Laser Lithotripsy", Lasers in Surgery and Medicine, 2010, pp. 232-236, Wiley-Liss Inc.

Varghese, B., "Influence of absorption induced thermal initiation pathway on irradiance threshold for laser induced breakdown", Biomedical Optics Express, 2015, vol. 6, No. 4, Optical Society of America.

Noack, J., "Influence of pulse duration on mechanical effects after laser-induced breakdown in water", Journal of Applied Physics, 1998, pp. 7488-EOA, vol. 83, American Institute of Physics.

Van Leeuwen, Ton G., et al. "Intraluminal Vapor Bubble Induced by Excimer Laser Pulse Causes Microsecond Arterial Dilation and Invagination Leading to Extensive Wall Damage in the Rabbit", Circulation, Apr. 1993, vol. 87, No. 4, American Heart Association, Dallas, TX, USA.

Accucoat, "Beamsplitter: Divide, combine & conquer"; 2023.

Lin et al., "Photoacoustic imaging", Science Direct; 2021.

(56) References Cited

OTHER PUBLICATIONS

Zhou et al., "Photoacoustic Imaging with fiber optic technology: A review", Science Direct; 2020.
International Search Report and Written Opinion issued by the European Patent Office, for Serial No. PCT/US2022/053775, dated Apr. 21, 2023.
International Search Report and Written Opinion issued by the European Patent Office, for Serial No. PCT US2023/011497, dated Apr. 28, 2023.
International Search Report and Written Opinion issued by the European Patent Office, for Serial No. PCT/US2023/012599, dated May 19, 2023.
Vogel, A., et al. "Intraocular Photodisruption With Picosecond and Nanosecond Laser Pulses: Tissue Effects in Cornea, Lens, and Retina", Investigative Ophthalmology & Visual Science, Jun. 1994, pp. 3032-3044, vol. 35, No. 7, Association for Research in Vision and Ophthalmology.
Jones, H. M., et al. "Pulsed dielectric breakdown of pressurized water and salt solutions", Journal of Applied Physics, Jun. 1998, pp. 795-805, vol. 77, No. 2, American Institute of Physics.
Kozulin, I., et al. "The dynamic of the water explosive vaporization on the flat microheater", Journal of Physics: Conference Series, 2018, pp. 1-4, IOP Publishing, Russia.
Cross, F., "Laser Angioplasty", Vascular Medicine Review, 1992, pp. 21-30, Edward Arnold.
Doukas, A. G., et al. "Laser-generated stress waves and their effects on the cell membrane", IEEE Journal of Selected Topics in Quantum Electronics, 1999, pp. 997-1003, vol. 5, Issue 4, IEEE.
Noack, J., et al. "Laser-Induced Plasma Formation in Water at Nanosecond to Femtosecond Time Scales: Calculation of Thresholds, Absorption Coefficients, and Energy Density", IEEE Journal of Quantum Electronics, 1999, pp. 1156-1167, vol. 35, No. 8, IEEE.
Pratsos, A., "The use of Laser for the treatment of coronary artery disease", Bryn Mawr Hospital, 2010.
Li, Xian-Dong, et al. "Influence of deposited energy on shock wave induced by underwater pulsed current discharge", Physics of Plasmas, 2016, vol. 23, American Institute of Physics.
Logunov, S., et al. "Light diffusing optical fiber illumination", Renewable Energy and the Environment Congress, 2013, Corning, NY, USA.
Maxwell, A. D., et al. "Cavitation clouds created by shock scattering from bubbles during histotripsy", Acoustical Society of America, 2011, pp. 1888-1898, vol. 130, No. 4, Acoustical Society of America.
Mcateer, James A., et al. "Ultracal-30 Gypsum Artificial Stones for Research on the Mechinisms of Stone Breakage in Shock Wave Lithotripsy", 2005, pp. 429-434, Springer-Verlag.
Vogel, A., et al. "Mechanisms of Intraocular Photodisruption With Picosecond and Nanosecond Laser Pulses", Lasers in Surgery and Medicine, 1994, pp. 32-43, vol. 15, Wiley-Liss Inc., Lubeck, Germany.
Vogel, A., et al. "Mechanisms of Pulsed Laser Ablation of Biological Tissues", Chemical Reviews, 2003, pp. 577-644, vol. 103, No. 2, American Chemical Society.
Medlight, "Cylindrical light diffuser Model RD-ML", Medlight S.A., Switzerland. 2015.
Medlight, "Cylindircal light diffuser Model RD", Medlight S.A., Switzerland. 2015.
Mayo, Michael E., "Interaction of Laser Radiation with Urinary Calculi", Cranfield University Defense and Security, PhD Thesis, 2009, Cranfield University.
Vogel, A., et al. "Minimization of Cavitation Effects in Pulsed Laser Ablation Illustrated on Laser Angioplasty", Applied Physics, 1996, pp. 173-182, vol. 62, Springer-Verlag.
Mirshekari, G., et al. "Microscale Shock Tube", Journal of Microelectromechanical Systems, 2012, pp. 739-747, vol. 21, No. 3, IEEE.
"Polymicro Sculpted Silica Fiber Tips", Molex, 2013, Molex.
Zhou, J., et al. "Optical Fiber Tips and Their Applications", Polymicro Technologies A Subsidiary of Molex, Nov. 2007.
Liang, Xiao-Xuan, et al. "Multi-Rate-Equation modeling of the energy spectrum of laser-induced conduction band electrons in water", Optics Express, 2019, vol. 27, No. 4, Optical Society of America.
Nachabe, R., et al. "Diagnosis of breast cancer using diffuse optical spectroscopy from 500 to 1600 nm: comparison of classification methods", Journal of Biomedical Optics, 2011, vol. 16(8), SPIE.
Naugol'nykh, K. A., et al. "Spark Discharges in Water", Academy of Sciences USSR Institute of Acoustics, 1971, Nauka Publishing Co., Moscow, USSR.
Van Leeuwen, Ton G., et al. "Noncontact Tissue Ablation by Holmium: YSGG Laser Pulses in Blood", Lasers in Surgery and Medicine, 1991, vol. 11, pp. 26-34, Wiley-Liss Inc.
Nyame, Yaw A., et al. "Kidney Stone Models for In Vitro Lithotripsy Research: A Comprehensive Review", Journal of Endourology, Oct. 2015, pp. 1106-1109, vol. 29, No. 10, Mary Ann Liebert Inc., Cleveland, USA.
Ohl, Siew-Wan, et al. "Bubbles with shock waves and ultrasound: a review", Interface Focus, pp. 1-15, vol. 5, The Royal Society Publishing. Oct. 2015.
Zheng, W., "Optical Lenses Manufactured on Fiber Ends", IEEE, 2015, Splicer Engineering, Duncan SC USA.
Dwyer, P. J., et al. "Optically integrating balloon device for photodynamic therapy", Lasers in Surgery and Medicine, 2000, pp. 58-66, vol. 26, Issue 1, Wiley-Liss Inc., Boston MA USA.
"The New Optiguide DCYL700 Fiber Optic Diffuser Series", Optiguide Fiber Optic Spec Sheet, Pinnacle Biologics, 2014, Pinnacle Biologics, Illinois, USA.
Van Leeuwen, Ton G., et al. "Origin of arterial wall dissections induced by pulsed excimer and mid-infared laser ablation in the pig", JACC, 1992, pp. 1610-1618, vol. 19, No. 7, American College of Cardiology.
Oshita, D., et al. "Characteristic of Cavitation Bubbles and Shock Waves Generated by Pulsed Electric Discharges with Different Voltages", IEEE, 2012, pp. 102-105, Kumamoto, Japan.
Karsch, Karl R., et al. "Percutaneous Coronary Excimer Laser Angioplasty in Patients With Stable and Unstable Angina Pectoris", Circulation, 1990, pp. 1849-1859, vol. 81, No. 6, American Heart Association, Dallas TX, USA.
Murray, A., et al. "Peripheral laser angioplasty with pulsed dye laser and ball tipped optical fibres", The Lancet, 1989, pp. 1471-1474, vol. 2, Issue 8678-8679.
Mohammadzadeh, M., et al. "Photoacoustic Shock Wave Emission and Cavitation from Structured Optical Fiber Tips", Applied Physics Letters, 2016, vol. 108, American Institute of Physics Publishing LLC.
Doukas, A. G., et al. "Physical characteristics and biological effects of laser-induced stress waves", Ultrasound in Medicine and Biology, 1996, pp. 151-164, vol. 22, Issue 2, World Federation for Ultrasound in Medicine and Biology, USA.
Doukas, A. G., et al. "Physical factors involved in stress-wave-induced cell injury: the effect of stress gradient", Ultrasound in Medicine and Biology, 1995, pp. 961-967, vol. 21, Issue 7, Elsevier Science Ltd., USA.
Piedrahita, Francisco S., "Experimental Research Work on a Sub-Millimeter Spark-Gap for Sub Nanosecond Gas Breakdown", Thesis for Universidad Nacional De Colombia, 2012, Bogota, Colombia.
Vogel, A., et al. "Plasma Formation in Water by Picosecond and Nanosecond Nd: YAG Laser Pulses—Part I: Optical Breakdown at Threshold and Superthreshold Irradiance", IEEE Journal of Selected Topics in Quantum Electronics, 1996, pp. 847-859, vol. 2, No. 4, IEEE.
Park, Hee K., et al. "Pressure Generation and Measurement in the Rapid Vaporization of Water on a Pulsed-Laser-Heated Surface", Journal of Applied Physics, 1996, pp. 4072-4081, vol. 80, No. 7, American Institute of Physics.
Cummings, Joseph P., et al. "Q-Switched laser ablation of tissue: plume dynamics and the effect of tissue mechanical properties", SPIE, Laser-Tissue Interaction III, 1992, pp. 242-253, vol. 1646.
Lee, Seung H., et al. "Radial-firing optical fiber tip containing conical-shaped air-pocket for biomedical applications", Optics Express, 2015, vol. 23, No. 16, Optical Society of America.

(56) References Cited

OTHER PUBLICATIONS

Hui, C., et al. "Research on sound fields generated by laser-induced liquid breakdown", Optica Applicata, 2010, pp. 898-907, vol. XL, No. 4, Xi'an, China.

Riel, Louis-Philippe, et al. "Characterization of Calcified Plaques Retrieved From Occluded Arteries and Comparison with Potential Artificial Analogues", Proceedings of the ASME 2014 International Mechanical Engineering Congress and Exposition, 2014, pp. 1-11, ASME, Canada.

Roberts, Randy M., et al. "The Energy Partition of Underwater Sparks", The Journal of the Acoustical Society of America, 1996, pp. 3465-3475, vol. 99, No. 6, Acoustical Society of America.

Rocha, R., et al. "Fluorescence and Reflectance Spectroscopy for Identification of Atherosclerosis in Human Carotid Arteries Using Principal Components Analysis", Photomedicine and Lsser Surgery, 2008, pp. 329-335, vol. 26, No. 4, Mary Ann Liebert Inc.

Scepanovic, Obrad R., et al. "Multimodal spectroscopy detects features of vulnerable atherosclerotic plaque", Journal of Biomedical Optics, 2011, pp. 1-10, vol. 16, No. 1, SPIE.

Serruys, P. W., et al. "Shaking and Breaking Calcified Plaque Lithoplasty, a Breakthrough in Interventional Armamentarium?", JACC: Cardiovascular Imaging, 2017, pp. 907-911, vol. 10, No. 8, Elsevier.

Vogel, A., et al. "Shock wave emission and cavitation bubble generation by picosecond and nanosecond optical breakdown in water", The Journal of the Acoustical Society of America, 1996, pp. 148-165, vol. 100, No. 1, Acoustical Society of America.

Vogel, A., et al. "Shock-Wave Energy and Acoustic Energy Dissipation After Laser-induced Breakdown", SPIE, 1998, pp. 180-189, vol. 3254, SPIE.

International Search Report and Written Opinion, issued by the EP/ISA, in PCT/US2021/048819, dated Jan. 14, 2022.

International Search Report and Written Opinion, PCT Application Serial No. PCT/US2022/047751 dated Feb. 10, 2023, by the European Patent Office.

Stelzle, F., et al. "Diffuse Reflectance Spectroscopy for Optical Soft Tissue Differentiation as Remote Feedback Control for Tissue-Specific Laser Surgery", Lasers in Surgery and Medicine, 2010, pp. 319-325, vol. 42, Wiley-Liss Inc.

Stelzle, F., et al. Tissue Discrimination by Uncorrected Autofluorescence Spectra: A Proof-of-Principle Study for Tissue-Specific Laser Surgery, Sensors, 2013, pp. 13717-13731, vol. 13, Basel, Switzerland.

Tagawa, Y., et al. "Structure of laser-induced shock wave in water", Japan Society for the Promotion of Science, 2016.

Shen, Y., et al. "Theoretical and experimental studies of directivity of sound field generated by pulsed laser induced breakdown in liquid water", SPIE, 2013, pp. 8796141-8796148, vol. 8796, SPIE.

Preisack, M., et al. "Ultrafast imaging of tissue ablation by a XeCl excimer laser in saline", Lasers in Surgery and Medicine, 1992, pp. 520-527, vol. 12, Wiley-Liss Inc.

Versluis, M., et al. "How Snapping Shrimp Snap: Through Cavitating Bubbles", Science Mag, 2000, pp. 2114-2117, vol. 289, American Association for the Advancement of Science, Washington DC, USA.

Yan, D., et al. "Study of the Electrical Characteristics, Shock-Wave Pressure Characteristics, and Attenuation Law Based on Pulse Discharge in Water", Shock and Vibration, 2016, pp. 1-11, vol. 2016, Article ID 6412309, Hindawi Publishing Corporation.

Zhang, Q., et al. "Improved Instruments and Methods for the Photographic Study of Spark-Induced Cavitation Bubbles", Water, 2018, pp. 1-12, vol. 10, No. 1683.

"Damage threshold of fiber facets", NKT Photonics, 2012, pp. 1-4, Denmark.

Smith, A., et al. "Bulk and surface laser damage of silica by picosecond and nanosecond pulses at 1064 nm", Applied Optics, 2008, pp. 4812-4832, vol. 47, No. 26, Optical Society of America.

Smith, A., et al. "Deterministic Nanosecond Laser-Induced Breakdown Thresholds In Pure and Yb3 Doped Fused Silica", SPIE, 2007, pp. 6453171-64531712, vol. 6453, SPIE.

Sun, X., et al. "Laser Induced Damage to Large Core Optical Fiber by High Peak Power Laser", Specialty Photonics Division, 2010.

Smith, A., et al. "Nanosecond laser-induced breakdown in pure and Yb3 doped fused silica", SPIE, 2007, vol. 6403, SPIE.

Smith, A., et al. "Optical Damage Limits to Pulse Energy From Fibers", IEEE Journal of Selected Topics in Quantum Electronics, 2009, pp. 153-158, vol. 15, No. 1, IEEE.

Reichel, E., et al. "A Special Irrigation Liquid to Increase the Reliability of Laser-Induced Shockwave Lithotripsy", Lasers in Surgery and Medicine, 1992, pp. 204-209, vol. 12, Wiley-Liss Inc., Graz, Austria.

Reichel, E., et al. "Bifunctional irrigation liquid as an ideal energy converter for laser lithotripsy with nanosecond aser pulses", SPIE Lasers in Urology, Laparoscopy, and General Surgery, 1991, pp. 129-133, vol. 1421, SPIE.

Reichel, E., et al. "Laser-induced Shock Wave Lithotripsy with a Regenerative Energy Converter", Lasers in Medical Science, 1992, pp. 423-425, vol. 7, Bailliere Tindall.

Hardy, L., et al. "Cavitation Bubble Dynamics during Thulium Fiber Laser Lithotripsy", SPIE BiOS, 2016, vol. 9689, SPIE.

Deckelbaum, L., "Coronary Laser Angioplasty", Lasers in Surgery and Medicine, 1994, pp. 101-110, vol. 14, Wiley-Liss Inc., Conneticuit, USA.

Shangguan, H., et al. "Effects of Material Properties on Laser-induced Bubble Formation in Absorbing Liquids and on Submerged Targets", Diagnostic and Therapeutic Cardiovascular Interventions VII, SPIE, 1997, pp. 783-791, vol. 2869, SPIE.

Van Leeuwen, T., et al. "Excimer Laser Induced Bubble: Dimensions, Theory, and Implications for Laser Angioplasty", Lasers in Surgery and Medicine, 1996, pp. 381-390, vol. 18, Wiley-Liss Inc., The Netherlands.

Vogel, A., et al. "Shock Wave Emission and Cavitation Bubble Generation by Picosecond and Nanosecond Optical Breakdown in Water", The Journal of Acoustical Society of America, 1996, pp. 148-165, vol. 100, No. 1, The Acoustical Society of America.

Reichel, E., et al. "Bifunctional irrigation liquid as an ideal energy converter for laser lithotripsy with nanosecond laser pulses", SPIE Lasers in Urology, Laparoscopy, and General Surgery, 1991, pp. 129-133, vol. 1421, SPIE.

Varghese, B., et al. "Influence of absorption induced thermal initiation pathway on irradiance threshold for laser Induced breakdown", Biomedical Optics Express, 2015, vol. 6, No. 4, Optical Society of America.

Linz, N., et al. "Wavelength dependence of nanosecond infrared laser-induced breakdown in water: Evidence for multiphoton initiation via an intermediate state", Physical Review, 2015, pp. 134114.1-1341141.10, vol. 91, American Physical Society.

International Search Report and Written Opinion dated Jun. 27, 2018, in PCT Application Serial No. PCT/US2018/027121.

International Search Report and Written Opinion dated Jul. 20, 2018, in PCT Application Serial No. PCT/US2018/027801.

International Search Report and Written Opinion dated Jul. 20, 2018, in PCT Application Serial No. PCT/US2018/027784.

European Search Report, for European U.S. Appl. No. 18/185,152, dated Dec. 13, 2018.

International Search Report and Written Opinion dated May 22, 2019, in PCT Application Serial No. PCT/US2019/022009.

International Search Report and Written Opinion dated May 29, 2019, in PCT Application Serial No. PCT/US2019/022016.

International Search Report and Written Opinion dated Jun. 22, 2018, in Application Serial No. NL2019807, issued by the European Patent Office.

Noimark, Sacha, et al., "Carbon-Nanotube-PDMS Composite Coatings on Optical Fibers for All-Optical Ultrasound Imaging", Advanced Functional Materials, 2016, pp. 8390-8396, vol. 26, Wiley-Liss Inc.

Chen, Sung-Liang, "Review of Laser-Generated Ultrasound Transmitters and their Applications to All-Optical Ultrasound Transducers and Imaging", Appl. Sci. 2017, 7, 25.

Colchester, R., et al. "Laser-Generated ultrasound with optica fibres using functionalised carbon nanotube composite coatings", Appl. Phys. Lett., 2014, vol. 104, 173504, American Institute of Physics.

(56) References Cited

OTHER PUBLICATIONS

Poduval, R., et al. "Optical fiber ultrasound transmitter with electrospun carbon nanotube-polymer composite", Appl. Phys. Lett., 2017, vol. 110, 223701, American Institute of Physics.

Tian, J., et al. "Distributed fiber-optic laser-ultrasound generation based on ghost-mode of tilted fiber Bragg gratings", Optics Express, Mar. 2013, pp. 6109-6114, vol. 21, No. 5, Optical Society of America.

Kim, J., et al. "Optical Fiber Laser-Generated-Focused-Ultrasound Transducers for Intravascular Therapies", IEEE, 2017.

Kang, H., et al. "Enhanced photocoagulation with catheter-based diffusing optical device", Journal of Biomedical Optics, 2012, vol. 17, Issue 11, 118001, SPIE.

International Search Report and Written Opinion dated Jan. 3, 2020, in PCT Application Serial No. PCT/US2019/056579.

Communication Pursuant to Article 94(3) EPC, for European Patent Application No. 18185152.8, dated Jan. 16, 2019.

European Search Report, for European Patent Application No. 18185152.8, dated Dec. 20, 2018.

International Search Report and Written Opinion dated Jul. 29, 2020 in PCT Application Serial No. PCT/US2020/034005.

International Search Report and Written Opinion dated Sep. 11, 2020 in PCT Application Serial No. PCT/US2020/038517.

International Search Report and Written Opinion dated Sep. 9, 2020 in PCT Application Serial No. PCT/US2020/038530.

International Search Report and Written Opinion dated Sep. 11, 2020 in PCT Application Serial No. PCT/US2020/038521.

International Search Report and Written Opinion dated Sep. 7, 2020 in PCT Application Serial No. PCT/US2020/034642.

PathFinder Digital, "Free Space Optics vs. Fiber Optics", 2023.

International Search Report and Written Opinion, issued in Application Serial No. PCT/US2023/016152, dated Jul. 12, 2023.

* cited by examiner

OPTICAL EMITTER HOUSING ASSEMBLY FOR INTRAVASCULAR LITHOTRIPSY DEVICE

RELATED APPLICATIONS

This application claims priority on U.S. Provisional Application Ser. No. 63/289,294, filed on Dec. 14, 2021, and entitled "OPTICAL EMITTER HOUSING ASSEMBLY FOR INTRAVASCULAR LITHOTRIPSY DEVICE", and on U.S. Provisional Application Ser. No. 63/335,131, filed on Apr. 26, 2022, and entitled "OPTICAL EMITTER HOUSING ASSEMBLY FOR INTRAVASCULAR LITHOTRIPSY DEVICE". As far as permitted, the contents of U.S. Provisional Application Ser. Nos. 63/289,294 and 63/335,131, are incorporated in their entirety herein by reference.

BACKGROUND

Vascular lesions (also referred to herein as a "treatment site") within vessels in the body can be associated with an increased risk for major adverse events, such as myocardial infarction, embolism, deep vein thrombosis, stroke, and the like. Severe vascular lesions, such as severely calcified vascular lesions, can be difficult to treat and achieve patency for a physician in a clinical setting.

Vascular lesions may be treated using interventions such as drug therapy, balloon angioplasty, atherectomy, stent placement, vascular graft bypass, to name a few. Such interventions may not always be ideal or may require subsequent treatment to address the lesion.

Intravascular lithotripsy is one method that has been recently used with some success for breaking up vascular lesions within vessels in the body. Intravascular lithotripsy utilizes a combination of pressure waves and bubble dynamics that are generated intravascularly in a fluid-filled balloon catheter. In particular, during an intravascular lithotripsy treatment, a high energy source is used to generate plasma and ultimately pressure waves as well as a rapid bubble expansion within a fluid-filled balloon to crack calcification at a treatment site within the vasculature that includes one or more vascular lesions. The associated rapid bubble formation from the plasma initiation and resulting localized fluid velocity within the balloon transfers mechanical energy through the incompressible fluid to impart a fracture force on the intravascular calcium, which is opposed to the balloon wall. The rapid change in fluid momentum upon hitting the balloon wall is known as hydraulic shock, or water hammer.

It is desired to more accurately and precisely direct and/or concentrate energy generated within the fluid-filled balloon so as to impart pressure onto and induce fractures at a treatment site within or adjacent to a blood vessel wall.

There is an ongoing desire to enhance vessel patency and optimization of therapy delivery parameters within an intravascular lithotripsy catheter system in a manner that is consistently manufacturable.

SUMMARY

The present invention is directed toward a catheter system for placement within a blood vessel having a vessel wall. The catheter system can be used for treating a treatment site within or adjacent to the vessel wall or a heart valve within a body of a patient. In various embodiments, the catheter system includes an energy source, a catheter fluid, and an emitter assembly. The energy source generates energy. The emitter assembly includes (i) at least a portion of an energy guide having a guide distal end that is selectively positioned near the treatment site, (ii) a plasma generator, and (iii) an emitter housing that is secured to each of the energy guide and the plasma generator to maintain a relative position between the guide distal end of the energy guide and the plasma generator. The energy guide is configured to receive energy from the energy source and direct the energy toward the plasma generator to generate a plasma bubble in the catheter fluid. The plasma generator directs energy from the plasma bubble toward the treatment site.

In some embodiments, the emitter housing includes (i) a first housing section that is secured to the energy guide at or near the guide distal end, (ii) a second housing section that is one of secured to and integrally formed with the plasma generator, and (iii) a connector section that is coupled to and extends between the first housing section and the second housing section.

In certain embodiments, the first housing section is substantially cylindrical-shaped. In some such embodiments, the first housing section includes a small, housing gap that extends fully along a length of the first housing section and that allows for slight expansion or contraction of the first housing section due to changes in environmental conditions.

In certain embodiments, the first housing section includes a guide aperture; and at least a portion of the energy guide is secured within the guide aperture.

In some embodiments, the catheter system further includes adhesive material that is configured to secure the first housing section to the energy guide at or near the guide distal end.

In certain embodiments, the first housing section includes a first housing port through which the adhesive material can be provided between the first housing section and the energy guide so as to secure the first housing section to the energy guide at or near the guide distal end.

In some embodiments, the second housing section is substantially cylindrical-shaped.

In certain embodiments, the second housing section includes a small, housing gap that extends fully along a length of the second housing section and that allows for slight expansion or contraction of the second housing section due to changes in environmental conditions.

In certain embodiments, the second housing section includes a generator aperture; and at least a portion of the plasma generator is secured within the generator aperture.

In some embodiments, the catheter system further includes adhesive material that is configured to secure the second housing section to the plasma generator.

In certain embodiments, the second housing section includes a second housing port through which the adhesive material can be provided between the second housing section and the plasma generator so as to secure the second housing section to the plasma generator.

In other embodiments, the second housing section is integrally formed with the plasma generator.

In certain embodiments, the connector section includes a section opening; and the plasma generator directs the energy from the plasma bubble through the section opening and toward the treatment site.

In some embodiments, the connector section is partially cylindrical-shaped; and the section opening extends fully along a length of the connector section.

In some embodiments, the plasma generator has a proximal end that is angled so as to direct the energy from the plasma bubble through the section opening and toward the treatment site.

In certain embodiments, the proximal end of the plasma generator is angled at between approximately 5 degrees and 45 degrees relative to a flat, perpendicular configuration.

In some embodiments, the catheter system further includes a reinforcement cover that is positioned to substantially encircle the emitter housing.

In one embodiment, the reinforcement cover includes a polyimide tube.

In certain embodiments, the catheter system further includes a guidewire lumen that includes an outer surface having a groove; and the emitter housing is positioned within the groove formed along the outer surface of the guidewire lumen.

In some embodiments, the catheter system further includes a first assembly attacher that is positioned adjacent to the first housing section, and a second assembly attacher that is positioned adjacent to the second housing section, to hold the emitter housing within the groove formed along the outer surface of the guidewire lumen.

In some embodiments, the catheter system further includes a balloon including a balloon wall that defines a balloon interior, the balloon being configured to retain the catheter fluid within the balloon interior.

In various embodiments, the guide distal end, the plasma generator and the emitter housing are positioned within the balloon interior.

In certain such embodiments, the balloon is selectively inflatable with the catheter fluid to expand to an inflated state, and when the balloon is in the inflated state the balloon wall is configured to be positioned substantially adjacent to the treatment site.

In some embodiments, the plasma generator is configured to direct the energy from the plasma bubble toward a portion of the balloon wall that is positioned substantially adjacent to the treatment site.

In certain embodiments, the energy guide generates one or more pressure waves in the catheter fluid that impart a force upon the treatment site.

In some embodiments, the energy guide includes an optical fiber.

In various embodiments, the energy source includes a laser.

In certain embodiments, the catheter fluid includes one of a wetting agent and a surfactant.

The present invention is further directed toward a method for treating a treatment site within or adjacent to a blood vessel within a body of a patient, the method including the steps of: generating energy with an energy source; positioning an emitter assembly within a catheter fluid near the treatment site, the emitter assembly including (i) at least a portion of an energy guide having a guide distal end that is selectively positioned near the treatment site, (ii) a plasma generator, and (iii) an emitter housing that is secured to each of the energy guide and the plasma generator to maintain a relative position between the guide distal end of the energy guide and the plasma generator; receiving energy from the energy source with the energy guide; generating a plasma bubble in the catheter fluid with the energy from the energy guide that is directed toward the plasma generator; and directing energy from the plasma bubble with the plasma generator toward the treatment site.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope herein is defined by the appended claims and their legal equivalents.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

Figure 1:
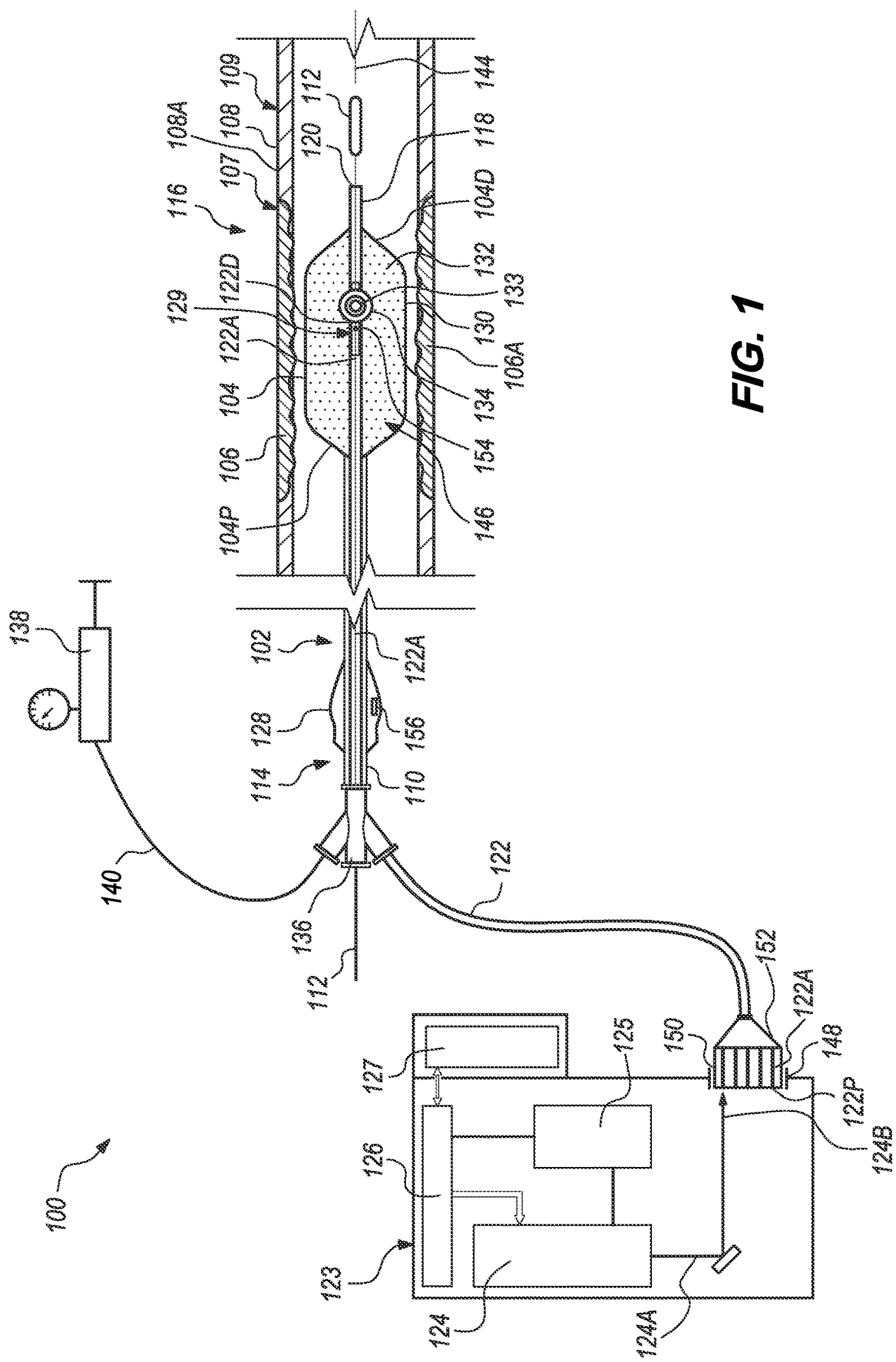
FIG. 1 is a simplified schematic cross-sectional view illustration of an embodiment of a catheter system in accordance with various embodiments, the catheter system including an emitter assembly that includes at least a portion of an energy guide.

While embodiments of the present invention are susceptible to various modifications and alternative forms, specifics thereof have been shown by way of example and drawings, and are described in detail herein. It is understood, however, that the scope herein is not limited to the particular embodiments described. On the contrary, the intention is to cover modifications, equivalents, and alternatives falling within the spirit and scope herein.

DESCRIPTION

Treatment of vascular lesions can reduce major adverse events or death in affected subjects. As referred to herein, a major adverse event is one that can occur anywhere within the body due to the presence of a vascular lesion. Major adverse events can include, but are not limited to, major adverse cardiac events, major adverse events in the peripheral or central vasculature, major adverse events in the brain, major adverse events in the musculature, or major adverse events in any of the internal organs.

In various embodiments, the catheter systems and related methods disclosed herein can include a catheter configured to advance to a vascular lesion, such as a calcified vascular lesion or a fibrous vascular lesion, at a treatment site located within or adjacent a blood vessel or a heart valve within a body of a patient. The catheter includes a catheter shaft, and an inflatable balloon that is coupled and/or secured to the catheter shaft. The balloon can include a balloon wall that defines a balloon interior. The balloon can be configured to receive a catheter fluid within the balloon interior to expand from a deflated state suitable for advancing the catheter through a patient's vasculature, to an inflated state suitable for anchoring the catheter in position relative to the treatment site.

As used herein, the terms "treatment site, "intravascular lesion" and "vascular lesion" are used interchangeably unless otherwise noted. As such, the intravascular lesions and/or the vascular lesions are sometimes referred to herein simply as "lesions".

Those of ordinary skill in the art will realize that the following detailed description of the present invention is illustrative only and is not intended to be in any way limiting. Other embodiments of the present invention will readily suggest themselves to such skilled persons having the benefit of this disclosure. Reference will now be made in detail to implementations of the present invention as illustrated in the accompanying drawings. The same or similar nomenclature and/or reference indicators will be used throughout the drawings and the following detailed description to refer to the same or like parts.

In the interest of clarity, not all of the routine features of the implementations described herein are shown and described. It is appreciated that in the development of any such actual implementation, numerous implementation-specific decisions must be made in order to achieve the developer's specific goals, such as compliance with application-related and business-related constraints, and that these specific goals will vary from one implementation to another and from one developer to another. Moreover, it is recognized that such a development effort might be complex and time-consuming, but would nevertheless be a routine undertaking of engineering for those of ordinary skill in the art having the benefit of this disclosure.

The catheter systems disclosed herein can include many different forms. Referring now to FIG. 1, a simplified schematic cross-sectional view illustration is shown of a catheter system 100 in accordance with various embodiments. The catheter system 100 is suitable for imparting pressure waves to induce fractures in one or more treatment sites within or adjacent a vessel wall of a blood vessel or adjacent to a heart valve within a body of a patient. In the embodiment illustrated in FIG. 1, the catheter system 100 can include one or more of a catheter 102, an energy guide bundle 122 including one or more energy guides 122A, a source manifold 136, a fluid pump 138, a system console 123 including one or more of an energy source 124, a power source 125, a system controller 126, and a graphic user interface 127 (a "GUI"), a handle assembly 128, and an emitter assembly 129. In various embodiments, the emitter assembly 129 includes and/or incorporates at least a portion of the energy guides 122A, and the emitter assembly 129 is configured to direct and/or concentrate energy toward one or more treatment sites 106A at a treatment site 106 within or adjacent to a vessel wall 108A of a blood vessel 108 or a heart valve within a body 107 of a patient 109. Alternatively, the catheter system 100 can include more components or fewer components than those specifically illustrated and described in relation to FIG. 1.

The catheter 102 is configured to move to the treatment site 106 within or adjacent to the vessel wall 108A of the blood vessel 108 or a heart valve within the body 107 of the patient 109. The treatment site 106 can include one or more vascular lesions 106A such as calcified vascular lesions, for example. Additionally, or in the alternative, the treatment site 106 can include vascular lesions 106A such as fibrous vascular lesions. Still alternatively, in some implementations, the catheter 102 can be used at a treatment site 106 within or adjacent to a heart valve within the body 107 of the patient 109.

The catheter 102 can include an inflatable balloon 104 (sometimes referred to herein simply as a "balloon"), a catheter shaft 110, and a guidewire 112. The balloon 104 can be coupled to the catheter shaft 110. The balloon 104 can include a balloon proximal end 104P and a balloon distal end 104D. The catheter shaft 110 can extend from a proximal portion 114 of the catheter system 100 to a distal portion 116 of the catheter system 100. The catheter shaft 110 can include a longitudinal axis 144. The catheter 102 and/or the catheter shaft 110 can also include a guidewire lumen 118 which is configured to move over the guidewire 112. As utilized herein, the guidewire lumen 118 defines a conduit through which the guidewire 112 extends. The catheter shaft 110 can further include an inflation lumen (not shown) and/or various other lumens for various other purposes. In some embodiments, the catheter 102 can have a distal end opening 120 and can accommodate and be tracked over the guidewire 112 as the catheter 102 is moved and positioned at or near the treatment site 106. In some embodiments, the balloon proximal end 104P can be coupled to the catheter shaft 110, and the balloon distal end 104D can be coupled to the guidewire lumen 118.

The balloon 104 includes a balloon wall 130 that defines a balloon interior 146. The balloon 104 can be selectively inflated with a catheter fluid 132 to expand from a deflated state suitable for advancing the catheter 102 through a patient's vasculature, to an inflated state (as shown in FIG. 1) suitable for anchoring the catheter 102 in position relative to the treatment site 106. Stated in another manner, when the balloon 104 is in the inflated state, the balloon wall 130 of the balloon 104 is configured to be positioned substantially adjacent to the treatment site 106. It is appreciated that although FIG. 1 illustrates the balloon wall 130 of the balloon 104 being shown spaced apart from the treatment site 106 of the blood vessel 108 or a heart valve when in the inflated state, this is done for ease of illustration. It is recognized that the balloon wall 130 of the balloon 104 will typically be substantially directly adjacent to and/or abutting the treatment site 106 when the balloon 104 is in the inflated state.

The balloon 104 suitable for use in the catheter system 100 includes those that can be passed through the vasculature of a patient 109 when in the deflated state. In some embodiments, the balloons 104 are made from silicone. In other embodiments, the balloon 104 can be made from materials such as polydimethylsiloxane (PDMS), polyurethane, polymers such as PEBAX™ material, nylon, or any other suitable material.

The balloon 104 can have any suitable diameter (in the inflated state). In various embodiments, the balloon 104 can have a diameter (in the inflated state) ranging from less than one millimeter (mm) up to 25 mm. In some embodiments, the balloon 104 can have a diameter (in the inflated state) ranging from at least 1.5 mm up to 14 mm. In some embodiments, the balloon 104 can have a diameter (in the inflated state) ranging from at least two mm up to five mm.

In some embodiments, the balloon 104 can have a length ranging from at least three mm to 300 mm. More particularly, in some embodiments, the balloon 104 can have a length ranging from at least eight mm to 200 mm. It is appreciated that a balloon 104 having a relatively longer length can be positioned adjacent to larger treatment sites 106, and, thus, may be usable for imparting pressure waves onto and inducing fractures in larger vascular lesions 106A or multiple vascular lesions 106A at precise locations within the treatment site 106. It is further appreciated that a longer balloon 104 can also be positioned adjacent to multiple treatment sites 106 at any one given time.

The balloon 104 can be inflated to inflation pressures of between approximately one atmosphere (atm) and 70 atm. In some embodiments, the balloon 104 can be inflated to inflation pressures of from at least 20 atm to 60 atm. In other embodiments, the balloon 104 can be inflated to inflation pressures of from at least six atm to 20 atm. In still other embodiments, the balloon 104 can be inflated to inflation pressures of from at least three atm to 20 atm. In yet other embodiments, the balloon 104 can be inflated to inflation pressures of from at least two atm to ten atm.

The balloon 104 can have various shapes, including, but not to be limited to, a conical shape, a square shape, a rectangular shape, a spherical shape, a conical/square shape, a conical/spherical shape, an extended spherical shape, an oval shape, a tapered shape, a bone shape, a stepped diameter shape, an offset shape, or a conical offset shape. In some embodiments, the balloon 104 can include a drug eluting coating or a drug eluting stent structure. The drug eluting coating or drug eluting stent can include one or more therapeutic agents including anti-inflammatory agents, anti-neoplastic agents, anti-angiogenic agents, and the like.

The catheter fluid 132 can be a liquid or a gas. Some examples of the catheter fluid 132 suitable for use can include, but are not limited to one or more of water, saline, contrast medium, fluorocarbons, perfluorocarbons, gases, such as carbon dioxide, or any other suitable catheter fluid 132. In some embodiments, the catheter fluid 132 can be used as a base inflation fluid. In some embodiments, the catheter fluid 132 can include a mixture of saline to contrast medium in a volume ratio of approximately 50:50. In other embodiments, the catheter fluid 132 can include a mixture of saline to contrast medium in a volume ratio of approximately 25:75. In still other embodiments, the catheter fluid 132 can include a mixture of saline to contrast medium in a volume ratio of approximately 75:25. However, it is understood that any suitable ratio of saline to contrast medium can be used. The catheter fluid 132 can be tailored on the basis of composition, viscosity, and the like so that the rate of travel of the pressure waves are appropriately manipulated. In certain embodiments, the catheter fluids 132 suitable for use are biocompatible. A volume of catheter fluid 132 can be tailored by the chosen energy source 124 and the type of catheter fluid 132 used.

In certain embodiments, the catheter fluid 132 can include a wetting agent or surface-active agent (surfactant). These compounds can lower the tension between solid and liquid matter. These compounds can act as emulsifiers, dispersants, detergents, and water infiltration agents. Wetting agents or surfactants reduce surface tension of the liquid and allow it to fully wet and come into contact with optical components (such as the energy guide(s) 122A) and mechanical components (such as other portions of the emitter assembly(s) 129). This reduces or eliminates the accumulation of bubbles and pockets or inclusions of gas within the emitter assembly 129. Nonexclusive examples of chemicals that can be used as wetting agents include, but are not limited to, Benzalkonium Chloride, Benzethonium Chloride, Cetylpyridinium Chloride, Poloxamer 188, Poloxamer 407, Polysorbate 20, Polysorbate 40, and the like. Non-exclusive examples of surfactants can include, but are not limited to, ionic and non-ionic detergents, and Sodium stearate. Another suitable surfactant is 4-(5-dodecyl) benzenesulfonate. Other examples can include docusate (dioctyl sodium sulfosuccinate), alkyl ether phosphates, and perfluorooctanesulfonate (PFOS), to name a few.

By using a wetting agent or surfactant, direct liquid contact with the energy guide 122A allows the energy to be more efficiently converted into a plasma. Using the wetting agent or surfactant with the small dimensions of the optical and mechanical components used in the emitter assembly 129 and other parts of the catheter 102, it is less difficult to achieve greater (or complete) wetting. Decreasing the surface tension of the liquid can decrease the difficulty for such small structures to be effectively wetted by the liquid and therefore be nearly or completely immersed. By reducing or eliminating air or other gas bubbles from adhering to the optical and mechanical structure and energy guides 122A, considerable increase in efficiency of the device can occur.

The specific percentage of the wetting agent or surfactant can be varied to suit the design parameters of the catheter system 100 and/or the emitter assembly 129 being used. In one embodiment, the percentage of the wetting agent or surfactant can be less than approximately 50% by volume of the catheter fluid 132. In non-exclusive alternative embodiments, the percentage of the wetting agent or surfactant can be less than approximately 40%, 30%, 20%, 10%, 5%, 2%, 1%, 0.1% or 0.01% by volume of the catheter fluid 132. Still alternatively, the percentage of the wetting agent or surfactant can fall outside of the foregoing ranges.

In some embodiments, the contrast agents used in the contrast media can include, but are not to be limited to, iodine-based contrast agents, such as ionic or non-ionic iodine-based contrast agents. Some non-limiting examples of ionic iodine-based contrast agents include diatrizoate, metrizoate, iothalamate, and ioxaglate. Some non-limiting examples of non-ionic iodine-based contrast agents include iopamidol, iohexol, ioxilan, iopromide, iodixanol, and ioversol. In other embodiments, non-iodine-based contrast agents can be used. Suitable non-iodine containing contrast agents can include gadolinium (III)-based contrast agents. Suitable fluorocarbon and perfluorocarbon agents can include, but are not to be limited to, agents such as the perfluorocarbon dodecafluoropentane (DDFP, C5F12).

The catheter fluids 132 can include those that include absorptive agents that can selectively absorb light in the ultraviolet region (e.g., at least ten nanometers (nm) to 400 nm), the visible region (e.g., at least 400 nm to 780 nm), or the near-infrared region (e.g., at least 780 nm to 2.5 μm) of the electromagnetic spectrum. Suitable absorptive agents can include those with absorption maxima along the spectrum from at least ten nm to 2.5 μm. Alternatively, the catheter fluids 132 can include those that include absorptive agents that can selectively absorb light in the mid-infrared region (e.g., at least 2.5 μm to 15 μm), or the far-infrared region (e.g., at least 15 μm to one mm) of the electromagnetic spectrum. In various embodiments, the absorptive agent can be those that have an absorption maximum matched with the emission maximum of the laser used in the catheter system 100. By way of non-limiting examples, various lasers usable in the catheter system 100 can include neodymium:yttrium-aluminum-garnet (Nd:YAG–emission maximum=1064 nm) lasers, holmium:YAG (Ho:YAG–emission maximum=2.1 μm) lasers, or erbium:YAG (Er:YAG–emission maximum=2.94 μm) lasers. In some embodiments, the absorptive agents can be water-soluble. In other embodiments, the absorptive agents are not water-soluble. In some embodiments, the absorptive agents used in the catheter fluids 132 can be tailored to match the peak emission of the energy source 124. Various energy sources 124 having emission wavelengths of at least ten nanometers to one millimeter are discussed elsewhere herein.

The catheter shaft 110 of the catheter 102 can be coupled to the one or more energy guides 122A of the energy guide bundle 122 that are in optical communication with the energy source 124. The energy guide(s) 122A can be disposed along the catheter shaft 110 and within the balloon 104. In some embodiments, each energy guide 122A can be an optical fiber and the energy source 124 can be a laser. The energy source 124 can be in optical communication with the energy guides 122A at the proximal portion 114 of the catheter system 100.

In some embodiments, the catheter shaft 110 can be coupled to multiple energy guides 122A such as a first energy guide, a second energy guide, a third energy guide, etc., which can be disposed at any suitable positions about and/or relative to the guidewire lumen 118 and/or the catheter shaft 110. For example, in certain non-exclusive embodiments, two energy guides 122A can be spaced apart by approximately 180 degrees about the circumference of the guidewire lumen 118 and/or the catheter shaft 110; three energy guides 122A can be spaced apart by approximately 120 degrees about the circumference of the guidewire lumen 118 and/or the catheter shaft 110; or four energy guides 122A can be spaced apart by approximately 90 degrees about the circumference of the guidewire lumen 118 and/or the catheter shaft 110. Still alternatively, multiple energy guides 122A need not be uniformly spaced apart from one another about the circumference of the guidewire lumen 118 and/or the catheter shaft 110. More particularly, it is further appreciated that the energy guides 122A can be disposed uniformly or non-uniformly about the guidewire lumen 118 and/or the catheter shaft 110 to achieve the desired effect in the desired locations.

In certain embodiments, the guidewire lumen 118 can have a grooved outer surface, with the grooves extending in a generally longitudinal direction along the guidewire lumen 118. In such embodiments, each of the energy guides 122A and/or the emitter assembly(s) 129 can be positioned, received and retained within an individual groove formed along and/or into the outer surface of the guidewire lumen 118. Alternatively, the guidewire lumen 118 can be formed without a grooved outer surface, and the position of the energy guides 122A and/or the emitter assembly(s) 129 relative to the guidewire lumen 118 can be maintained in another suitable manner.

The catheter system 100 and/or the energy guide bundle 122 can include any number of energy guides 122A in optical communication with the energy source 124 at the proximal portion 114, and with the catheter fluid 132 within the balloon interior 146 of the balloon 104 at the distal portion 116. For example, in some embodiments, the catheter system 100 and/or the energy guide bundle 122 can include from one energy guide 122A to greater than 30 energy guides 122A. Alternatively, in other embodiments, the catheter system 100 and/or the energy guide bundle 122 can include greater than 30 energy guides 122A.

The energy guides 122A can have any suitable design for purposes of generating plasma and/or pressure waves in the catheter fluid 132 within the balloon interior 146. Thus, the general description of the energy guides 122A as light guides is not intended to be limiting in any manner, except for as set forth in the claims appended hereto. More particularly, although the catheter systems 100 are often described with the energy source 124 as a light source and the one or more energy guides 122A as light guides, the catheter system 100 can alternatively include any suitable energy source 124 and energy guides 122A for purposes of generating the desired plasma in the catheter fluid 132 within the balloon interior 146. For example, in one non-exclusive alternative embodiment, the energy source 124 can be configured to provide high voltage pulses, and each energy guide 122A can include an electrode pair including spaced apart electrodes that extend into the balloon interior 146. In such embodiment, each pulse of high voltage is applied to the electrodes and forms an electrical arc across the electrodes, which, in turn, generates the plasma and forms the pressure waves in the catheter fluid 132 that are utilized to provide the fracture force onto the vascular lesions 106A at the treatment site 106. Still alternatively, the energy source 124 and/or the energy guides 122A can have another suitable design and/or configuration.

In certain embodiments, the energy guides 122A can include an optical fiber or flexible light pipe. The energy guides 122A can be thin and flexible and can allow light signals to be sent with very little loss of strength. The energy guides 122A can include a core surrounded by a cladding about its circumference. In some embodiments, the core can be a cylindrical core or a partially cylindrical core. The core and cladding of the energy guides 122A can be formed from one or more materials, including but not limited to one or more types of glass, silica, or one or more polymers. The energy guides 122A may also include a protective coating, such as a polymer. It is appreciated that the index of refraction of the core will be greater than the index of refraction of the cladding.

Each energy guide 122A can guide energy along its length from a guide proximal end 122P to the guide distal end 122D having at least one optical window (not shown) that is positioned within the balloon interior 146.

The energy guides 122A can assume many configurations about and/or relative to the catheter shaft 110 of the catheter 102. In some embodiments, the energy guides 122A can run parallel to the longitudinal axis 144 of the catheter shaft 110. In some embodiments, the energy guides 122A can be physically coupled to the catheter shaft 110. In other embodiments, the energy guides 122A can be disposed along a length of an outer diameter of the catheter shaft 110. In yet other embodiments, the energy guides 122A can be disposed within one or more energy guide lumens within the catheter shaft 110.

The energy guides 122A can also be disposed at any suitable positions about the circumference of the guidewire lumen 118 and/or the catheter shaft 110, and the guide distal end 122D of each of the energy guides 122A can be disposed at any suitable longitudinal position relative to the length of the balloon 104 and/or relative to the length of the guidewire lumen 118 to more effectively and precisely impart pressure waves for purposes of disrupting the vascular lesions 106A at the treatment site 106.

In certain embodiments, the energy guides 122A can include one or more photoacoustic transducers 154, where each photoacoustic transducer 154 can be in optical communication with the energy guide 122A within which it is disposed. In some embodiments, the photoacoustic transducers 154 can be in optical communication with the guide distal end 122D of the energy guide 122A. In such embodiments, the photoacoustic transducers 154 can have a shape that corresponds with and/or conforms to the guide distal end 122D of the energy guide 122A.

The photoacoustic transducer 154 is configured to convert light energy into an acoustic wave at or near the guide distal end 122D of the energy guide 122A. The direction of the acoustic wave can be tailored by changing an angle of the guide distal end 122D of the energy guide 122A.

In certain embodiments, the photoacoustic transducers 154 disposed at the guide distal end 122D of the energy guide 122A can assume the same shape as the guide distal end 122D of the energy guide 122A. For example, in certain non-exclusive embodiments, the photoacoustic transducer 154 and/or the guide distal end 122D can have a conical shape, a convex shape, a concave shape, a bulbous shape, a square shape, a stepped shape, a half-circle shape, an ovoid shape, and the like. The energy guide 122A can further include additional photoacoustic transducers 154 disposed along one or more side surfaces of the length of the energy guide 122A.

In some embodiments, the energy guides 122A and/or the emitter assembly 129 can further include one or more diverting features or "diverters" (not shown in FIG. 1), such as within the energy guide 122A and/or near the guide distal end 122D of the energy guide 122A, that are configured to direct energy from the energy guide 122A toward a side surface which can be located at or near the guide distal end 122D of the energy guide 122A, before the energy is directed toward the balloon wall 130. A diverting feature can include any feature of the system that diverts energy from the energy guide 122A away from its axial path toward a side surface of the energy guide 122A. The energy guides 122A can each include one or more optical windows disposed along the longitudinal or circumferential surfaces of each energy guide 122A and in optical communication with a diverting feature. Stated in another manner, the diverting features can be configured to direct energy in the energy guide 122A toward a side surface that is at or near the guide distal end 122D, where the side surface is in optical communication with an optical window. The optical windows can include a portion of the energy guide 122A that allows energy to exit the energy guide 122A from within the energy guide 122A, such as a portion of the energy guide 122A lacking a cladding material on or about the energy guide 122A.

Examples of the diverting features suitable for use include a reflecting element, a refracting element, and a fiber diffuser. The diverting features suitable for focusing energy away from the tip of the energy guides 122A can include, but are not to be limited to, those having a convex surface, a gradient-index (GRIN) lens, and a mirror focus lens. Upon contact with the diverting feature, the energy is diverted within the energy guide 122A to one or more of a plasma generator 133 and the photoacoustic transducer 154 that is in optical communication with a side surface of the energy guide 122A. When utilized, the photoacoustic transducer 154 then converts light energy into an acoustic wave that extends away from the side surface of the energy guide 122A.

Additionally, or in the alternative, in certain embodiments, such diverting features that can be incorporated into the energy guides 122A, can also be incorporated into the design of the emitter assembly 129 and/or the plasma generator 133 for purposes of directing and/or concentrating acoustic and mechanical energy toward specific areas of the balloon wall 130 in contact with the vascular lesions 106A at the treatment site 106 to impart pressure onto and induce fractures in such vascular lesions 106A.

The source manifold 136 can be positioned at or near the proximal portion 114 of the catheter system 100. The source manifold 136 can include one or more proximal end openings that can receive the one or more energy guides 122A of the energy guide bundle 122, the guidewire 112, and/or an inflation conduit 140 that is coupled in fluid communication with the fluid pump 138. The catheter system 100 can also include the fluid pump 138 that is configured to inflate the balloon 104 with the catheter fluid 132 as needed.

As noted above, in the embodiment illustrated in FIG. 1, the system console 123 includes one or more of the energy source 124, the power source 125, the system controller 126, and the GUI 127. Alternatively, the system console 123 can include more components or fewer components than those specifically illustrated in FIG. 1. For example, in certain non-exclusive alternative embodiments, the system console 123 can be designed without the GUI 127. Still alternatively, one or more of the energy source 124, the power source 125, the system controller 126, and the GUI 127 can be provided within the catheter system 100 without the specific need for the system console 123.

As shown, the system console 123, and the components included therewith, is operatively coupled to the catheter 102, the energy guide bundle 122, and the remainder of the catheter system 100. For example, in some embodiments, as illustrated in FIG. 1, the system console 123 can include a console connection aperture 148 (also sometimes referred to generally as a "socket") by which the energy guide bundle 122 is mechanically coupled to the system console 123. In such embodiments, the energy guide bundle 122 can include a guide coupling housing 150 (also sometimes referred to generally as a "ferrule") that houses a portion, such as the guide proximal end 122P, of each of the energy guides 122A. The guide coupling housing 150 is configured to fit and be selectively retained within the console connection aperture 148 to provide the mechanical coupling between the energy guide bundle 122 and the system console 123.

The energy guide bundle 122 can also include a guide bundler 152 (or "shell") that brings each of the individual energy guides 122A closer together so that the energy guides 122A and/or the energy guide bundle 122 can be in a more compact form as it extends with the catheter 102 into the blood vessel 108 or a heart valve during use of the catheter system 100.

The energy source 124 can be selectively and/or alternatively coupled in optical communication with each of the energy guides 122A, such as to the guide proximal end 122P of each of the energy guides 122A, in the energy guide bundle 122. In particular, the energy source 124 is configured to generate energy in the form of a source beam 124A, such as a pulsed source beam, that can be selectively and/or alternatively directed to and received by each of the energy guides 122A in the energy guide bundle 122 as an individual guide beam 124B. Alternatively, the catheter system 100 can include more than one energy source 124. For example, in one non-exclusive alternative embodiment, the catheter system 100 can include a separate energy source 124 for each of the energy guides 122A in the energy guide bundle 122.

The energy source 124 can have any suitable design. In certain embodiments, the energy source 124 can be configured to provide sub-millisecond pulses of energy from the energy source 124 that are focused onto a small spot in order to couple it into the guide proximal end 122P of the energy guide 122A. Such pulses of energy are then directed and/or guided along the energy guides 122A to a location within the balloon interior 146 of the balloon 104, thereby inducing plasma formation in the catheter fluid 132 within the balloon interior 146 of the balloon 104, such as via the plasma generator 133 that can be located at or near the guide distal end 122D of the energy guide 122A. In particular, in such embodiments, the energy emitted at the guide distal end 122D of the energy guide 122A is directed toward and energizes the plasma generator 133 to form the plasma in the catheter fluid 132 within the balloon interior 146. The plasma formation causes rapid bubble formation, and imparts pressure waves upon the treatment site 106. An exemplary plasma-induced bubble 134 is illustrated in FIG. 1.

In various non-exclusive alternative embodiments, the sub-millisecond pulses of energy from the energy source 124 can be delivered to the treatment site 106 at a frequency of between approximately one hertz (Hz) and 5000 Hz, between approximately 30 Hz and 1000 Hz, between approximately ten Hz and 100 Hz, or between approximately one Hz and 30 Hz. Alternatively, the sub-millisecond pulses of energy can be delivered to the treatment site 106 at a frequency that can be greater than 5000 Hz or less than one Hz, or any other suitable range of frequencies.

It is appreciated that although the energy source 124 is typically utilized to provide pulses of energy, the energy source 124 can still be described as providing a single source beam 124A, i.e. a single pulsed source beam.

The energy sources 124 suitable for use can include various types of light sources including lasers and lamps. Alternatively, the energy sources 124 can include any suitable type of energy source.

Suitable lasers can include short pulse lasers on the sub-millisecond timescale. In some embodiments, the energy source 124 can include lasers on the nanosecond (ns) timescale. The lasers can also include short pulse lasers on the picosecond (ps), femtosecond (fs), and microsecond (us) timescales. It is appreciated that there are many combinations of laser wavelengths, pulse widths and energy levels that can be employed to achieve plasma in the catheter fluid 132 of the catheter 102. In various non-exclusive alternative embodiments, the pulse widths can include those falling within a range including from at least ten ns to 3000 ns, at least 20 ns to 100 ns, or at least one ns to 500 ns. Alternatively, any other suitable pulse width range can be used.

Exemplary nanosecond lasers can include those within the UV to IR spectrum, spanning wavelengths of about ten nanometers (nm) to one millimeter (mm). In some embodiments, the energy sources 124 suitable for use in the catheter systems 100 can include those capable of producing light at wavelengths of from at least 750 nm to 2000 nm. In other embodiments, the energy sources 124 can include those capable of producing light at wavelengths of from at least 700 nm to 3000 nm. In still other embodiments, the energy sources 124 can include those capable of producing light at wavelengths of from at least 100 nm to ten micrometers (μm). Nanosecond lasers can include those having repetition rates of up to 200 kHz.

In some embodiments, the laser can include a Q-switched thulium:yttrium-aluminum-garnet (Tm:YAG) laser. In other embodiments, the laser can include a neodymium:yttrium-aluminum-garnet (Nd:YAG) laser, holmium:yttrium-aluminum-garnet (Ho:YAG) laser, erbium:yttrium-aluminum-garnet (Er:YAG) laser, excimer laser, helium-neon laser, carbon dioxide laser, as well as doped, pulsed, fiber lasers.

In still other embodiments, the energy source 124 can include a plurality of lasers that are grouped together in series. In yet other embodiments, the energy source 124 can include one or more low energy lasers that are fed into a high energy amplifier, such as a master oscillator power amplifier (MOPA). In still yet other embodiments, the energy source 124 can include a plurality of lasers that can be combined in parallel or in series to provide the energy needed to create the plasma bubble 134 in the catheter fluid 132.

The catheter system 100 can generate pressure waves having maximum pressures in the range of at least one megapascal (MPa) to 100 MPa. The maximum pressure generated by a particular catheter system 100 will depend on the energy source 124, the absorbing material, the bubble expansion, the propagation medium, the balloon material, and other factors. In various non-exclusive alternative embodiments, the catheter systems 100 can generate pressure waves having maximum pressures in the range of at least approximately two MPa to 50 MPa, at least approximately two MPa to 30 MPa, or approximately at least 15 MPa to 25 MPa.

The pressure waves can be imparted upon the treatment site 106 from a distance within a range from at least approximately 0.1 millimeters (mm) to greater than approximately 25 mm extending radially from the energy guides 122A when the catheter 102 is placed at the treatment site 106. In various non-exclusive alternative embodiments, the pressure waves can be imparted upon the treatment site 106 from a distance within a range from at least approximately ten mm to 20 mm, at least approximately one mm to ten mm, at least approximately 1.5 mm to four mm, or at least approximately 0.1 mm to ten mm extending radially from the energy guides 122A when the catheter 102 is placed at the treatment site 106. In other embodiments, the pressure waves can be imparted upon the treatment site 106 from another suitable distance that is different than the foregoing ranges. In some embodiments, the pressure waves can be imparted upon the treatment site 106 within a range of at least approximately two MPa to 30 MPa at a distance from at least approximately 0.1 mm to ten mm. In some embodiments, the pressure waves can be imparted upon the treatment site 106 from a range of at least approximately two MPa to 25 MPa at a distance from at least approximately 0.1 mm to ten mm. Still alternatively, other suitable pressure ranges and distances can be used.

The power source 125 is electrically coupled to and is configured to provide necessary power to each of the energy source 124, the system controller 126, the GUI 127, and the handle assembly 128. The power source 125 can have any suitable design for such purposes.

The system controller 126 is electrically coupled to and receives power from the power source 125. The system controller 126 is coupled to and is configured to control operation of each of the energy source 124 and the GUI 127. The system controller 126 can include one or more processors or circuits for purposes of controlling the operation of at least the energy source 124 and the GUI 127. For example, the system controller 126 can control the energy source 124 for generating pulses of energy as desired and/or at any desired firing rate.

The system controller 126 can also be configured to control operation of other components of the catheter system 100 such as the positioning of the catheter 102 adjacent to the treatment site 106, the inflation of the balloon 104 with the catheter fluid 132, etc. Further, or in the alternative, the catheter system 100 can include one or more additional controllers that can be positioned in any suitable manner for purposes of controlling the various operations of the catheter system 100. For example, in certain embodiments, an additional controller and/or a portion of the system controller 126 can be positioned and/or incorporated within the handle assembly 128.

The GUI 127 is accessible by the user or operator of the catheter system 100. The GUI 127 is electrically connected to the system controller 126. With such design, the GUI 127 can be used by the user or operator to ensure that the catheter system 100 is effectively utilized to impart pressure onto and induce fractures into the vascular lesions 106A at the treatment site 106. The GUI 127 can provide the user or operator with information that can be used before, during and after use of the catheter system 100. In one embodiment, the GUI 127 can provide static visual data and/or information to the user or operator. In addition, or in the alternative, the GUI 127 can provide dynamic visual data and/or information to the user or operator, such as video data or any other data that changes over time during use of the catheter system 100. In various embodiments, the GUI 127 can include one or more colors, different sizes, varying brightness, etc., that may act as alerts to the user or operator. Additionally, or in the alternative, the GUI 127 can provide audio data or information to the user or operator. The specifics of the GUI 127 can vary depending upon the design requirements of the catheter system 100, or the specific needs, specifications and/or desires of the user or operator.

As shown in FIG. 1, the handle assembly 128 can be positioned at or near the proximal portion 114 of the catheter system 100, and/or near the source manifold 136. In this embodiment, the handle assembly 128 is coupled to the balloon 104 and is positioned spaced apart from the balloon 104. Alternatively, the handle assembly 128 can be positioned at another suitable location.

The handle assembly 128 is handled and used by the user or operator to operate, position and control the catheter 102. The design and specific features of the handle assembly 128 can vary to suit the design requirements of the catheter system 100. In the embodiment illustrated in FIG. 1, the handle assembly 128 is separate from, but in electrical and/or fluid communication with one or more of the system controller 126, the energy source 124, the fluid pump 138, and the GUI 127. In some embodiments, the handle assembly 128 can integrate and/or include at least a portion of the system controller 126 within an interior of the handle assembly 128. For example, as shown, in certain such embodiments, the handle assembly 128 can include circuitry 156 that can form at least a portion of the system controller 126. In one embodiment, the circuitry 156 can include a printed circuit board having one or more integrated circuits, or any other suitable circuitry. In an alternative embodiment, the circuitry 156 can be omitted, or can be included within the system controller 126, which in various embodiments can be positioned outside of the handle assembly 128, such as within the system console 123. It is understood that the handle assembly 128 can include fewer or additional components than those specifically illustrated and described herein.

In various implementations, the emitter assembly 129 is configured to maintain a desired positioning between the guide distal end 122D of the energy guide 122A and the plasma generator 133, and to direct and/or concentrate energy generated in the catheter fluid 132 within the balloon interior 146 so as to impart pressure onto and induce fractures in vascular lesions 106A at the treatment site 106 within or adjacent to a vessel wall 108A of a blood vessel 108 or a heart valve. More particularly, by effectively maintaining the desired positioning between the guide distal end 122D of the energy guide 122A and the plasma generator 133, and with the particular design features that may be incorporated into the emitter assembly 129, the emitter assembly 129 is configured to concentrate and direct acoustic and/or mechanical energy toward specific areas of the balloon wall 130 in contact with the vascular lesions 106A at the treatment site 106 to enhance the delivery of such energy to the treatment site 106. Thus, the emitter assembly 129 is able to effectively improve the efficacy of the catheter system 100.

It is appreciated that, in some embodiments, a separate emitter assembly 129 can be included with and/or incorporated into each individual energy guide 122A. Alternatively, in other embodiments, a single emitter assembly 129 can be configured to operate in conjunction with more than one energy guide 122A. Still alternatively, each energy guide 122A need not have an emitter assembly 129 incorporated therein or associated therewith.

The design of the emitter assembly 129 and/or the specific positioning of the emitter assembly 129 can be varied to suit the requirements of the catheter system 100. In various embodiments, the emitter assembly 129 can utilize and/or incorporate at least a portion of the energy guide 122A, such as a portion that includes the guide distal end 122D of the energy guide 122A.

Various alternative embodiments of the emitter assembly 129 are illustrated and described in detail herein below within subsequent Figures.

As with all embodiments illustrated and described herein, various structures may be omitted from the figures for clarity and ease of understanding. Further, the figures may include certain structures that can be omitted without deviating from the intent and scope of the invention.

Figure 2:
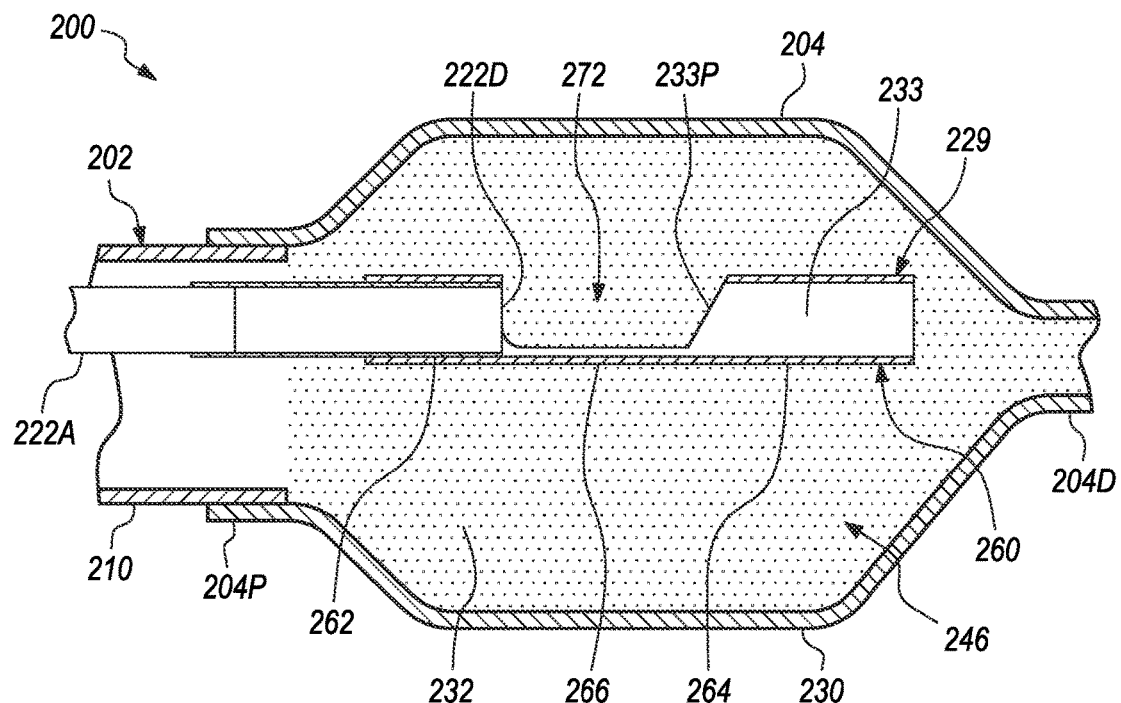
FIG. 2 is a simplified schematic cross-sectional view illustration of a portion of an embodiment of the catheter system including an embodiment of the emitter assembly.

FIG. 2 is a simplified schematic cross-sectional view illustration of a portion of an embodiment of the catheter system 200, including an embodiment of the emitter assembly 229. The design of the catheter system 200 can be varied. In various embodiments, as illustrated in FIG. 2, the catheter system 200 can include a catheter 202 including a catheter shaft 210; a balloon 204 having a balloon wall 230 that defines a balloon interior 246, a balloon proximal end 204P, and a balloon distal end 204D; and a catheter fluid 232 that is retained substantially within the balloon interior 246; and the emitter assembly 229, which in certain embodiments can incorporate at least a portion of an energy guide 222A. Alternatively, in other embodiments, the catheter system 200 can include more components or fewer components than what is specifically illustrated and described herein. For example, certain components that were illustrated in FIG. 1, such as the guidewire 112, the guidewire lumen 118, the source manifold 136, the fluid pump 138, the energy source 124, the power source 125, the system controller 126, the GUI 127, and the handle assembly 128, are not specifically illustrated in FIG. 2 for purposes of clarity, but would likely be included in any embodiment of the catheter system 200.

The design and function of the catheter shaft 210, the balloon 204, and the catheter fluid 232 are substantially similar to what was illustrated and described herein above. Accordingly, a detailed description of such components will not be repeated.

The balloon 204 is again selectively movable between a deflated state suitable for advancing the catheter 202 through a patient's vasculature, and an inflated state suitable for anchoring the catheter 202 in position relative to the treatment site 106 (illustrated in FIG. 1). In some embodiments, the balloon proximal end 204P can be coupled to the catheter shaft 210, and the balloon distal end 204D can be coupled to the guidewire lumen 118 (illustrated in FIG. 1). The balloon 204 can again be inflated with the catheter fluid 232, such as from the fluid pump 138 (illustrated in FIG. 1), that is directed into the balloon interior 246 of the balloon 204 via the inflation conduit 140 (illustrated in FIG. 1).

Similar to previous embodiments, the energy guide 222A can include one or more photoacoustic transducers 154

(illustrated in FIG. 1), where each photoacoustic transducer 154 can be in optical communication with the energy guide 222A within which it is disposed. In some embodiments, the photoacoustic transducers 154 can be in optical communication with the guide distal end 222D of the energy guide 222A. Alternatively, in other embodiments, the energy guide 222A can be designed without the one or more photoacoustic transducers 154.

In various embodiments, the emitter assembly 229 is configured to direct and/or concentrate energy generated in the catheter fluid 232 within the balloon interior 246 to impart pressure onto and induce fractures in vascular lesions 106A (illustrated in FIG. 1) at the treatment site 106. More particularly, the emitter assembly 229 is configured to direct and concentrate acoustic and/or mechanical energy toward specific areas of the balloon wall 230 that are in contact with the vascular lesions 106A at the treatment site 106 to enhance the delivery of such energy to the treatment site 106. As illustrated in this embodiment, at least some of the components of the emitter assembly 229 are positioned within the balloon interior 246

The design of the emitter assembly 229 can be varied. As shown in FIG. 2, in certain embodiments, the emitter assembly 229 includes at least a portion of the energy guide 222A, a plasma generator 233, and an emitter housing 260 that is coupled to and/or secured to the energy guide 222A and the plasma generator 233.

In some embodiments, as illustrated, the emitter housing 260 can include one or more of (i) a first housing section 262 that is coupled and/or secured to the energy guide 222A, such as at or near the guide distal end 222D of the energy guide 222A, (ii) a second housing section 264 that is coupled and/or secured to the plasma generator 233, and (iii) a connector section 266 that is coupled to, integrally formed with, and/or extends between the first housing section 262 and the second housing section 264. In such embodiments, the emitter housing 260 can be formed as a unitary structure that includes each of the first housing section 262, the second housing section 264 and the connector section 266; or the first housing section 262, the second housing section 264 and the connector section 266 of the emitter housing 260 can be formed as separate components that are secured to one another. Alternatively, the emitter housing 260 can include more components or fewer components than what is specifically illustrated in FIG. 2.

As shown, the first housing section 262 of the emitter housing 260 is configured to be secured to and substantially encircle at least a portion of the energy guide 222A, such as at or near the guide distal end 222D of the energy guide 222A. In one such embodiment, the first housing section 262 of the emitter housing 260 is substantially annular-shaped and/or cylindrical-shaped, and includes a guide aperture 362A (illustrated in FIG. 3) through and/or into which the energy guide 222A can be positioned. Alternatively, the first housing section 262 can have another suitable shape. As utilized herein, the description of the first housing section 262 as substantially encircling at least a portion of the energy guide 222A and/or being substantially annular-shaped and/or cylindrical-shaped is intended to signify that the first housing section 262 encircles at least approximately 90% to 95% of such portion of the energy guide 222A, but can further include a small housing gap 368 (illustrated in FIG. 3) that extends fully along a length of the first housing section 262 and that allows for slight expansion or contraction of the first housing section 262 due to changes in environmental conditions in which the catheter system 200 is being used. The housing gap 368 allows for such potential expansion or contraction of the first housing section 262 without adversely impacting the structure of the guide distal end 222D of the energy guide 222A about which the first housing section 262 is positioned.

The first housing section 262 can be secured to a portion of the energy guide 222A, such as at or near the guide distal end 222D, in any suitable manner. For example, the first housing section 262 can be secured to a portion of the energy guide 222A with any suitable type of adhesive material. Alternatively, the first housing section 262 can be secured to a portion of the energy guide 222A in another suitable manner.

Somewhat similarly, as shown, the second housing section 264 of the emitter housing 260 is configured to be secured to and substantially encircle the plasma generator 233. In one such embodiment, the second housing section 264 of the emitter housing 260 is substantially annular-shaped and/or cylindrical-shaped, and includes a generator aperture 364A (illustrated in FIG. 3) through and/or into which the plasma generator 233 can be positioned. Alternatively, the second housing section 264 can have another suitable shape. As utilized herein, the description of the second housing section 264 as substantially encircling the plasma generator 233 and/or being substantially annular-shaped and/or cylindrical-shaped is intended to signify that the second housing section 264 encircles at least approximately 90% to 95% of the plasma generator 233, but can further include a small housing gap 370 (illustrated in FIG. 3) that extends fully along a length of the second housing section 264 and that allows for slight expansion or contraction of the second housing section 264 due to changes in environmental conditions in which the catheter system 200 is being used. The housing gap 370 allows for such potential expansion or contraction of the second housing section 264 without adversely impacting the structure of the plasma generator 233 about which the second housing section 264 is positioned.

The second housing section 264 can be secured to the plasma generator 233 in any suitable manner. For example, the second housing section 264 can be secured to the plasma generator 233 with any suitable type of adhesive material. Alternatively, the second housing section 264 can be secured to the plasma generator 233 in another suitable manner.

The connector section 266 of the emitter housing 260, as noted, is coupled to, integrally formed with, and/or extends between the first housing section 262 and the second housing section 264. In some embodiments, the connector section 266 can be partially annular-shaped and/or cylindrical-shaped, with a section opening 272 that extends fully along a length of the connector section 266 to help define the less than complete annular and/or cylindrical shape of the connector section 266, and that is configured such that the plasma energy formed in the catheter fluid 232 within the balloon interior 246 is directed and/or concentrated through the section opening 272 and toward the vascular lesions 106A formed at the treatment site 106. The size and orientation of the section opening 272 can be varied depending on the size and position of the vascular lesions 106A being treated with the catheter system 200. In some non-exclusive alternative embodiments, the section opening 272 can be less than approximately 10%, 15%, 20%, 25%, 30%, 35%, 40%, 45%, 50%, 55%, 60%, 65%, 70%, 75%, 80%, 85% or 90% of what would otherwise form a complete annular and/or cylindrical shape for the connector section 266. Stated in another manner, the connector section 266 can be formed as at least approximately 90%, 85%, 80%, 75%, 70%, 65%, 60%, 55%, 50%, 45%, 40%, 35%, 30%, 25%, 20%, 15% or 10% of a complete annular-shaped and/or cylinder-shaped body.

In various embodiments, the emitter housing 260 can be formed from long, narrow tubing (a hypotube) and from any suitable materials. For example, in certain non-exclusive embodiments, the emitter housing 260 can be formed from a hypotube including one or more metals such as titanium, stainless steel, tungsten, etc. Alternatively, the emitter housing 260 may be formed from a hypotube including plastics such as polyimide and nylon. Still alternatively, the emitter housing 260 may be injection molded and over molding processing can be used to secure either the energy guide 222A and/or the plasma generator 233 into place. Yet alternatively, the emitter housing 260 can be formed in another suitable manner and/or from other suitable materials. For example, in certain alternative embodiments, the features on the emitter housing 260 can be done by laser cutting, milling or swiss screw machining processes of a raw hypotube.

With such design of the emitter housing 260, a desired relative positioning can be effectively maintained between the guide distal end 222D of the energy guide 222A and the plasma generator 233. During use of the catheter system 200, energy can be transmitted through the energy guide 222A and can be directed through the guide distal end 222D and toward the plasma generator 233 such that plasma can be generated in the catheter fluid 232 within the balloon interior 246 of the balloon 202. The guide distal end 222D can have any suitable shape such that the energy transmitted through the energy guide 222A can be effectively and accurately directed through the guide distal end 222D and toward the plasma generator 233. In one embodiment, the guide distal end 222D can have a flat, cleaved end through which the energy is directed toward the plasma generator 233. Alternatively, the guide distal end 222D can be generally semi-spherical, ball-shaped, conical, wedge-shaped, pyramidal or can be another suitable shape.

In some embodiments, as shown in FIG. 2, the plasma generator 233 (or target) can include a proximal end 233P that is angled or otherwise configured to more effectively direct and/or concentrate the energy in the form of the plasma that has been generated in the catheter fluid 232 through the section opening 272 in the connector section 266 of the emitter housing 260 and toward the balloon wall 230 positioned adjacent to the vascular lesions 106A at the treatment site 106. It is appreciated that the proximal end 233P of the plasma generator 233 can be configured at any suitable angle so as to effectively direct and/or concentrate the plasma energy as desired. For example, in some such embodiments, the proximal end 233P of the plasma generator 233 can be angled at between approximately 5 degrees and 45 degrees relative to a flat, perpendicular configuration. Alternatively, the proximal end 233P of the plasma generator 233 can be angled at less than 5 degrees or greater than 45 degrees relative to a flat, perpendicular configuration in order to direct energy in the form of the plasma that has been generated in the catheter fluid 232 toward the balloon wall 230 positioned adjacent to the treatment site 106.

The plasma generator 233 can be formed from any suitable materials. For example, in certain non-exclusive embodiments, the plasma generator 233 can be formed from one or more metals such as titanium, stainless steel, tungsten, etc. Alternatively, the plasma generator 233 may be formed from plastics such as polyimide and nylon. Still alternatively, the plasma generator 233 can be formed from other suitable materials. It is appreciated that in different embodiments, the plasma generator 233 can be formed from the same materials as the emitter housing 260 or different materials from the emitter housing 260.

It is appreciated that during use of the catheter system 200, the catheter fluid 232 that is utilized to inflate the balloon 204 also is allowed to enter into the area of the connector section 266 of the emitter housing 260 through the section opening 272. Subsequently, the pulsed energy that is directed through the energy guide 222A and toward the plasma generator 233 generates a plasma-induced bubble 134 (illustrated in FIG. 1) in the catheter fluid 232 in the general area of the connector section 266 of the emitter housing 260. As the bubble 134 expands, it is directed and/or focused by the proximal end 233P of the plasma generator 233 through the section opening 272 of the connector section 266 and toward the balloon wall 230 positioned adjacent to the vascular lesions 106A at the treatment site 106.

Figure 3:
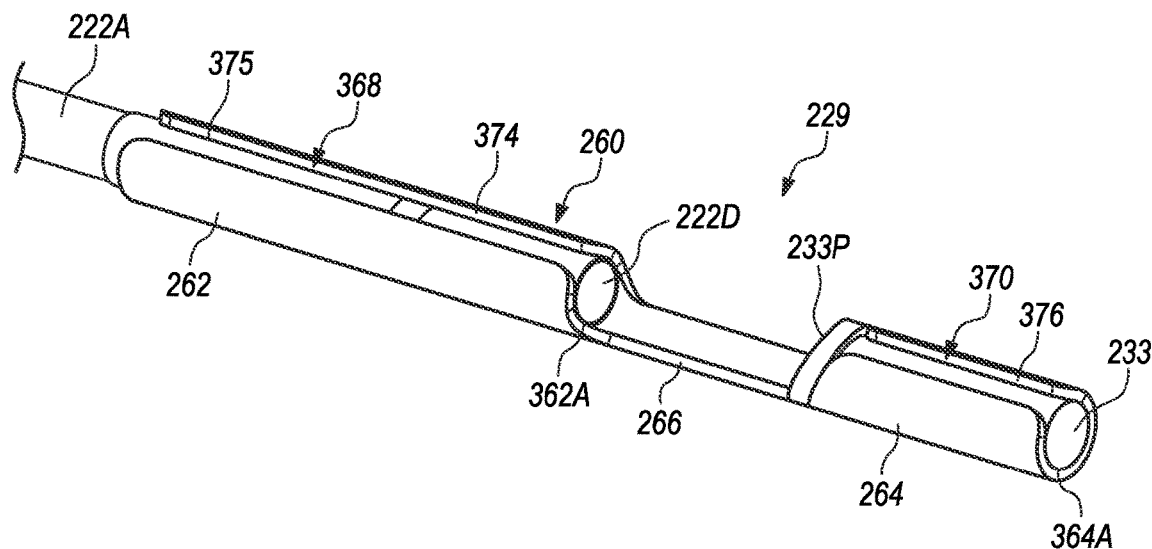
FIG. 3 is a simplified schematic perspective view illustration of the emitter assembly illustrated in FIG. 2.

FIG. 3 is a simplified schematic perspective view illustration of the emitter assembly 229 illustrated in FIG. 2. More particularly, FIG. 3 is a simplified schematic perspective view illustration showing a portion of the energy guide 222A, the plasma generator 233, and the emitter housing 260, including the first housing section 262, the second housing section 264, and the connector section 266, that together form the emitter assembly 229.

As shown, the first housing section 262 can be substantially annular-shaped and/or cylindrical-shaped, and can include the small housing gap 368 that that extends fully along a length of the first housing section 262 and that allows for slight expansion or contraction of the first housing section 262 due to changes in environmental conditions in which the catheter system 200 (illustrated in FIG. 2) is being used.

FIG. 3 also illustrates a first housing coupler 374 that is used for purposes of coupling the first housing section 262 to a portion of the energy guide 222A, such as at or near the guide distal end 222D of the energy guide 222A. The design of the first housing coupler 374 can be varied. For example, in one embodiment, the first housing coupler 374 can include an adhesive material that is positioned between an outer surface of the energy guide 222A and an inner surface of the first housing section 262 in order to effectively couple and/or secure the first housing section 262 to the energy guide 222A. Alternatively, the first housing coupler 374 can have another suitable design.

The type of adhesive materials used with the first housing coupler 374 for securing the first housing section 262 to the energy guide 222A can be varied. For example, in certain embodiments, adhesive materials with low hardness properties (such as silicone-based adhesives) may be chosen to dampen/lessen the shockwave force to the energy guide 222A. Alternatively, other suitable adhesive materials may be chosen.

In some embodiments, an extruded thermal plastic tubing (made from materials such as Pebax®, nylon, polyurethane, etc.) may be used to add a soft protective layer 375 between the energy guide 222A and the first housing section 262 of the emitter housing 260. Such protective layer 375 can also help to center the energy guide 222A in a manner that is slightly offset from the inner diameter of the emitter housing 260 to promote proper alignment with the plasma generator 233.

As illustrated, the second housing section 264 can be substantially annular-shaped and/or cylindrical-shaped, and can include the small housing gap 370 that that extends fully along a length of the second housing section 264 and that allows for slight expansion or contraction of the second housing section 264 due to changes in environmental conditions in which the catheter system 200 is being used.

FIG. 3 also illustrates a second housing coupler 376 that is used for purposes of coupling the second housing section 264 to the plasma generator 233. The design of the second housing coupler 376 can be varied. For example, in one embodiment, the second housing coupler 376 can include an adhesive material that is positioned between an outer surface of the plasma generator 233 and an inner surface of the second housing section 264 in order to effectively couple and/or secure the second housing section 264 to the plasma generator 233. It is appreciated that, in such embodiments, any suitable type of adhesive materials can be used for the second housing coupler 376. Alternatively, the second housing coupler 376 can have another suitable design and/or the second housing section 264 can be secured to the plasma generator 233 in another suitable manner. For example, a crimping process can crimp the plasma generator 233 mechanically in place within the second housing section 264. Still alternatively, the plasma generator 233 may also be press fit into the second housing section 264. Yet alternatively, the housing gap 368 may function as an expansion slot which may assist with an interference fit between the second housing section 264 and the plasma generator 233. The housing gap 368 or expansion slot may be made wide enough to minimize the outer diameter of the emitter housing to inner shaft, since it removes the wall thickness of the emitter housing 260 on the top end.

As further illustrated in FIG. 3, the generally flat, cleaved end of the guide distal end 222D faces across the connector section 266 of the emitter housing 260 toward the angled proximal end 233P of the plasma generator 233.

Figure 4:
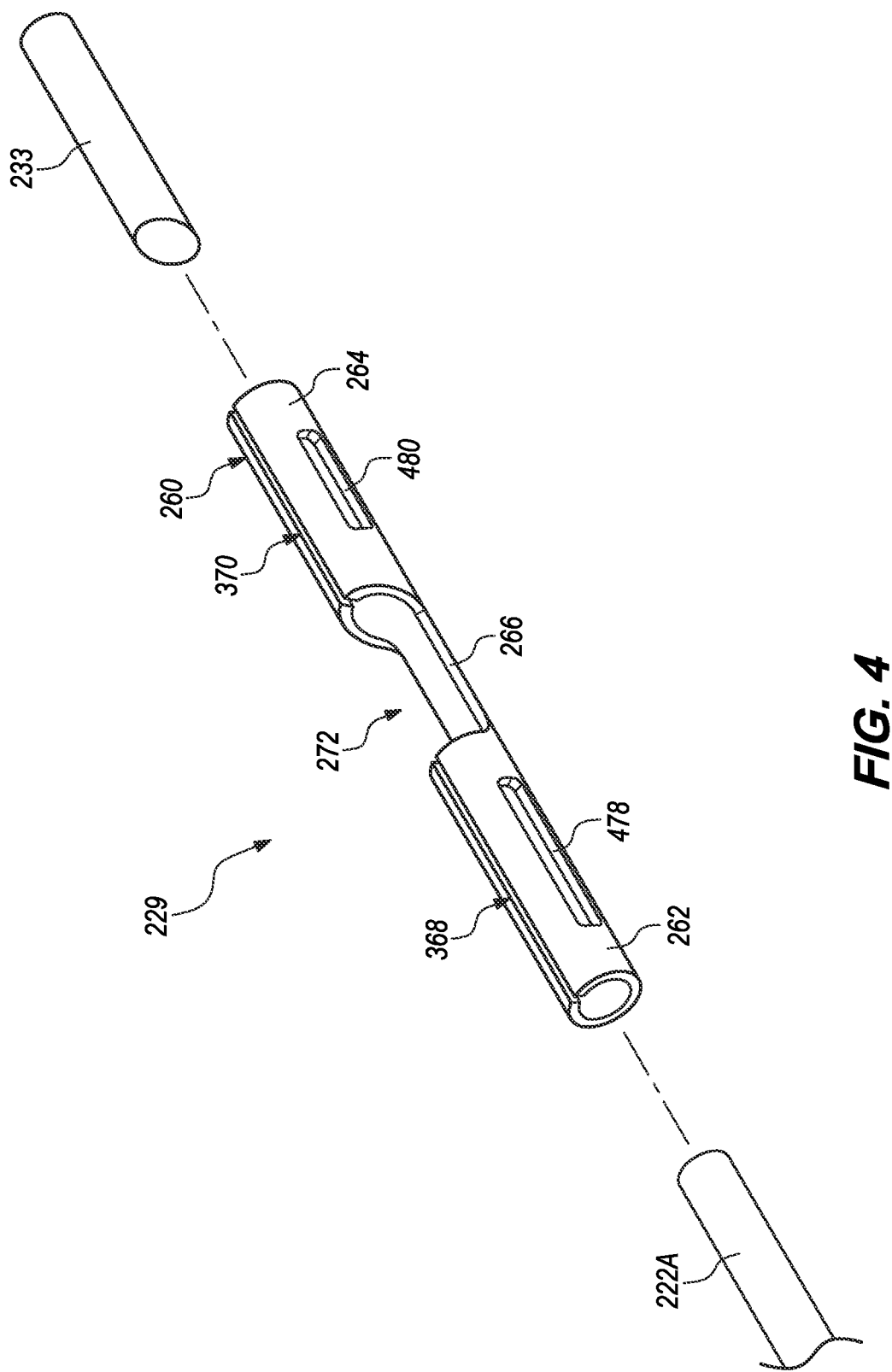
FIG. 4 is a simplified schematic exploded view illustration of the emitter assembly illustrated in FIG. 2.

FIG. 4 is a simplified schematic exploded view illustration of the emitter assembly 229 illustrated in FIG. 2. More particularly, FIG. 4 illustrates an exploded view of the emitter assembly 229 including at least a portion of the energy guide 222A, the plasma generator 233, and the emitter housing 260. FIG. 4 also illustrates the small housing gaps 368, 370 that can be formed into the first housing section 262 and the second housing section 264, respectively, of the emitter housing 260.

Also shown in FIG. 4 are (i) a first housing port 478 that is formed into the first housing section 262 of the emitter housing 260, through which an adhesive material can be introduced in order to effectively secure the first housing section 262 to a portion of the energy guide 222A, such as at or near the guide distal end 222D of the energy guide 222A; and (ii) a second housing port 480 that is formed into the second housing section 264 of the emitter housing 260, through which an adhesive material can be introduced in order to effectively secure the second housing section 264 to the plasma generator 233.

FIG. 4 also more clearly illustrates the shape of one embodiment of the connector section 266, including the section opening 272 through which the plasma energy can be directed toward the balloon wall 230 (illustrated in FIG. 2) that is positioned adjacent to the vascular lesions 106A (illustrated in FIG. 1) at the treatment site 106 (illustrated in FIG. 1).

Figure 5:
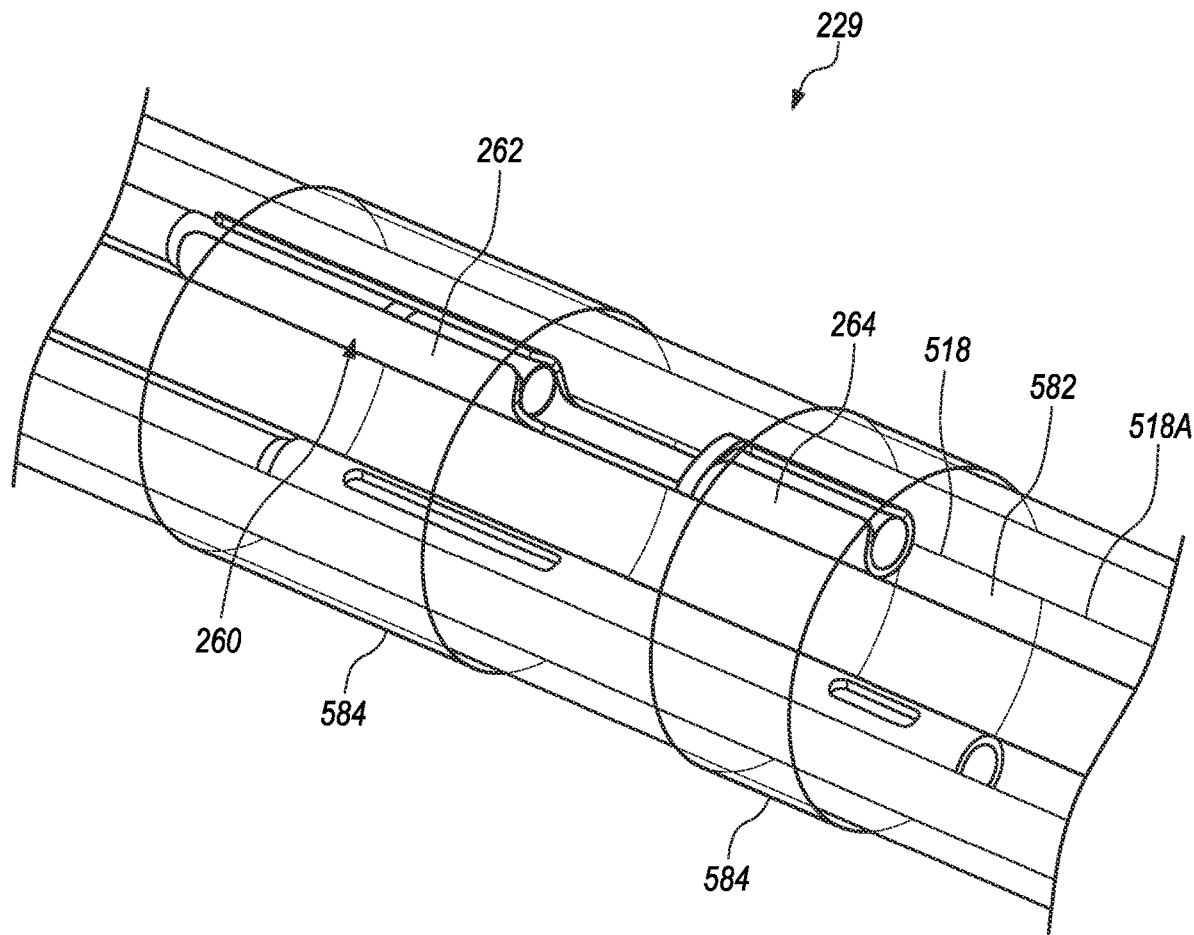
FIG. 5 is a simplified schematic perspective view illustration of the emitter assembly illustrated in FIG. 2 that is secured to a guidewire lumen of the catheter system.

FIG. 5 is a simplified schematic perspective view illustration of the emitter assembly 229 illustrated in FIG. 2 that is secured to a guidewire lumen 518 of the catheter system 200 (illustrated in FIG. 2).

As illustrated in this embodiment, the guidewire lumen 518 can include one or more grooves 582 that are formed along and/or into an outer surface 518A of the guidewire lumen 518. The emitter assembly 229 can then be positioned within one of the grooves 582 and can be held in position within the groove 582 by one or more assembly attachers 584 (two are illustrated in FIG. 5). As shown, a first assembly attacher 584 can be positioned substantially adjacent to the first housing section 262 of the emitter housing 260, and a second assembly attacher 584 can be positioned substantially adjacent to the second housing section 264 of the emitter housing 260, in order to effectively hold the emitter assembly 229 in position within the groove 582 formed into the outer surface 518A of the guidewire lumen 518.

The assembly attachers 584 can have any suitable design. In some embodiments, as shown in FIG. 5, the assembly attachers 584 can be provided in the form of a heat shrink-style attacher. Alternatively, the assembly attachers 584 can have another suitable design.

It is appreciated that a second emitter assembly 229 is also shown in FIG. 5 as being held in position within another one of the grooves 582 formed into the outer surface 518A of the guidewire lumen 518.

Figure 6:
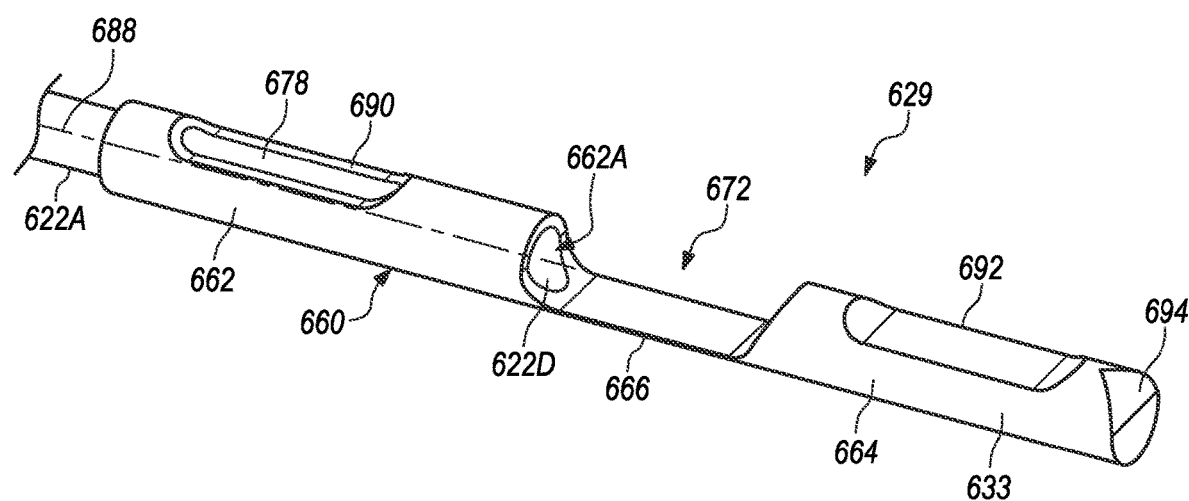
FIG. 6 is a simplified schematic perspective view illustration of another embodiment of the emitter assembly.

FIG. 6 is a simplified schematic perspective view illustration of another embodiment of the emitter assembly 629. As shown in FIG. 6, the emitter assembly 629 is somewhat similar in design, positioning and function to the previous embodiments. In this embodiment, the emitter assembly 629 again includes at least part of an energy guide 622A, a plasma generator 633, and an emitter housing 660. The emitter housing 660 again also includes (i) a first housing section 662, including a guide aperture 662A, that is configured to at least substantially encircle a portion of the energy guide 622A, such as at or near a guide distal end 622D of the energy guide 622A; (ii) a second housing section 664; and (iii) a connector section 666, again including a section opening 672, that is coupled to, integrally formed with and/or extends between the first housing section 662 and the second housing section 664. In this embodiment, the emitter assembly 629 is again configured to effectively direct and/or concentrate energy generated in the catheter fluid 232 (illustrated in FIG. 2) that is retained within the balloon 204 (illustrated in FIG. 2) so as to impart pressure onto and induce fractures in the vascular lesions 106A (illustrated in FIG. 1) at the treatment site 106 (illustrated in FIG. 1).

However, as shown in the embodiment illustrated in FIG. 6, the plasma generator 633 is integrally formed with the second housing section 664 of the emitter housing 660, rather than being positioned and/or secured substantially within the second housing section as in previous embodiments.

With such design, the emitter housing 660 can be fabricated by machining a single piece of rod using instead of making it out of a hypotube, as is typically used for the embodiment of the emitter housing 260 illustrated in FIG. 2. Machining the emitter housing 660 can be achieved through the use of any suitable machining processes. For example, in certain non-exclusive implementations, machining of the emitter housing 660 can be achieved by electrical discharge machining, or micro machining using milling or swiss screw machining techniques.

It is appreciated that there may be a few key advantages of this design as compared to a hypotube design. First, this integrated design where the emitter housing 660 is formed from a single piece of rod allows for the guide aperture 662A that is formed into the first housing section 662 and is configured to receive and retain the portion of the energy guide 622A to be offset an offset distance 786 (illustrated in FIG. 7) from a central axis 688 of the emitter housing 660, therefore allowing the connector section 666 to be thicker in dimension. Second, this integrated design maximizes the cross-sectional area of the plasma generator 633 since it is made out of the same material as the second housing section 664, whereas in the hypotube design the plasma generator material and hypotube material may be different, therefore the wall of the hypotube reduces the area of the plasma generator cross-section. It is desirable to maximize the cross-section of the plasma generator 633 to reduce the need for precise alignment of the guide distal end 622D of the energy guide 622A relative to the plasma generator 633. Third, as shown, the first housing section 662 and the second housing section 664 can include cut outs 690, 692, respectively, to accommodate the assembly attachers 584 (illustrated in FIG. 5), such as heat shrink-style attachers, pieced to the inner member shaft can be made to reduce crossing profile of the balloon catheter assembly. Fourth, in some embodiments, a first housing port 678, such as a glue port to accommodate the addition of adhesive material between the first housing section 662 and the energy guide 622A, can be combined with the cut out 690 in the first housing section 662 to allow adhesive to wick inside for consistent bonding. Fifth, radii 694 can be cut into the emitter housing 660 to reduce the number of sharp edges on the emitter housing 660, to inhibit potential damage to the balloon 204. Lastly, compared to the hypotube design, there is no need to bond a plasma generator into the emitter housing 660 since the plasma generator 633 is already integrated within the second housing section 664 of the emitter housing 660.

Figure 7:
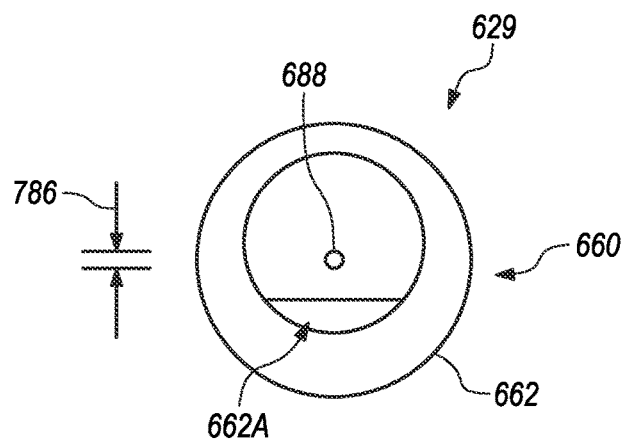
FIG. 7 is a simplified schematic end view illustration of a portion of the emitter assembly illustrated in FIG. 6.

FIG. 7 is a simplified schematic end view illustration of a portion of the emitter assembly 629 illustrated in FIG. 6. In particular, FIG. 7 is a simplified end view looking directly at the first housing section 662 of the emitter housing 660, which shows the guide aperture 662A that has been formed into the emitter housing 660 for purposes of receiving and retaining the portion of the energy guide 622A (illustrated in FIG. 6). As illustrated, the guide aperture 662A is offset an offset distance 786 from the central axis 688 (illustrated as a small circle) of the emitter housing 660, therefore allowing the connector section 666 (illustrated in FIG. 6) to be thicker in dimension. In certain non-exclusive embodiments, the guide aperture 662A can be offset from the central axis 688 of the emitter housing 660 by an offset distance 786 of between approximately 0.010 inches and 0.020 inches. In one such embodiment, the guide aperture 662A can be offset from the central axis 688 of the emitter housing 660 by an offset distance 786 of approximately 0.015 inches. Alternatively, the guide aperture 662A can be offset from the central axis 688 of the emitter housing 660 by an offset distance 786 of greater than 0.020 inches or less than 0.010 inches.

Figure 8:
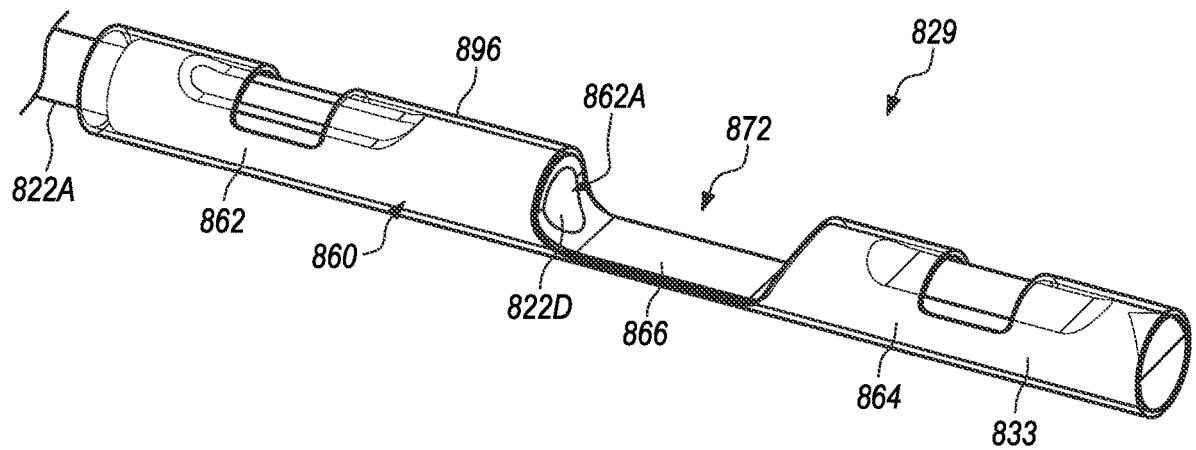
FIG. 8 is a simplified schematic perspective view illustration of still another embodiment of the emitter assembly.

FIG. 8 is a simplified schematic perspective view illustration of still another embodiment of the emitter assembly 829. In this embodiment, the emitter assembly 829 is again configured to effectively direct and/or concentrate energy generated in the catheter fluid 232 (illustrated in FIG. 2) that is retained within the balloon 204 (illustrated in FIG. 2) so as to impart pressure onto and induce fractures in the vascular lesions 106A (illustrated in FIG. 1) at the treatment site 106 (illustrated in FIG. 1).

As shown in FIG. 8, the emitter assembly 829 is somewhat similar in design, positioning and function to the embodiment illustrated in FIG. 6, and thus is able to realize most, if not all, of the same advantages noted above. For example, in this embodiment, the emitter assembly 829 again includes at least part of an energy guide 822A, a plasma generator 833, and an emitter housing 860. The emitter housing 860 again also includes (i) a first housing section 862, including a guide aperture 862A, that is configured to at least substantially encircle a portion of the energy guide 822A, such as at or near a guide distal end 822D of the energy guide 822A; (ii) a second housing section 864 that is integrally formed with the plasma generator 833; and (iii) a connector section 866, again including a section opening 872, that is coupled to, integrally formed with and/or extends between the first housing section 862 and the second housing section 864.

With such design, the emitter housing 860 can again be fabricated by machining a single piece of rod using instead of making it out of a hypotube, as is typically used for the embodiment of the emitter housing 260 illustrated in FIG. 2. Machining the emitter housing 860 can be achieved through the use of any suitable machining processes. For example, in certain non-exclusive implementations, machining of the emitter housing 860 can be achieved by electrical discharge machining, or micro machining using milling or swiss screw machining techniques.

However, as shown in the embodiment illustrated in FIG. 8, the emitter assembly 829 further includes a reinforcement cover 896 that is positioned about, placed over and/or substantially encircles the emitter housing 860. In some embodiments, the reinforcement cover 896 can be provided in the form of a polyimide tube, which, as shown, can be notched to match the design of the emitter housing 860, and is positioned about, placed over and/or substantially encircles the emitter housing 860 and bonded in place, such as with a UV cured adhesive. Alternatively, the reinforcement cover 896 can be formed from other materials and/or have another suitable design.

The reinforcement cover 896 serves to reinforce the structure of the solid emitter housing 860 and/or plasma generator 833 against the repetitive forces exerted during normal device function (acoustic pressure forces generated by the plasma initiation). Furthermore, in the event the solid emitter housing 860 and/or plasma generator 833 does become damaged, the reinforcement cover 896 can be further configured to contain any pieces or fragments that may be generated, thereby preventing them from becoming completely separated from the emitter housing 860.

As with previous embodiments, the emitter housing 860 and/or the plasma generator 833 can be formed from any suitable materials. For example, in some non-exclusive embodiments, the emitter housing 860 and/or the plasma generator 833 can be formed from one or more of metals such as titanium, stainless steel, tungsten, etc. Alternatively, the emitter housing 860 and/or the plasma generator 833 can be formed from other suitable materials.

It is further appreciated that, in certain non-exclusive alternative embodiments, the reinforcement cover 896 can also be utilized with one or more of the other embodiments of the emitter assembly illustrated and described in detail herein.

The present technology is also directed toward methods for treating a treatment site within or adjacent to a vessel wall, with such methods utilizing the devices disclosed herein.

It should be noted that, as used in this specification and the appended claims, the singular forms "a," "an," and "the" include plural referents unless the content and/or context clearly dictates otherwise. It should also be noted that the term "or" is generally employed in its sense including "and/or" unless the content or context clearly dictates otherwise.

It should also be noted that, as used in this specification and the appended claims, the phrase "configured" describes a system, apparatus, or other structure that is constructed or configured to perform a particular task or adopt a particular configuration. The phrase "configured" can be used interchangeably with other similar phrases such as arranged and configured, constructed and arranged, constructed, manufactured and arranged, and the like.

It is recognized that the figures shown and described are not necessarily drawn to scale, and that they are provided for ease of reference and understanding, and for relative positioning of the structures.

The headings used herein are provided for consistency with suggestions under 37 CFR 1.77 or otherwise to provide organizational cues. These headings shall not be viewed to limit or characterize the invention(s) set out in any claims that may issue from this disclosure. As an example, a description of a technology in the "Background" is not an admission that technology is prior art to any invention(s) in this disclosure. Neither is the "Summary" or "Abstract" to be considered as a characterization of the invention(s) set forth in issued claims.

The embodiments described herein are not intended to be exhaustive or to limit the invention to the precise forms disclosed in the following detailed description. Rather, the embodiments are chosen and described so that others skilled in the art can appreciate and understand the principles and practices. As such, aspects have been described with reference to various specific and preferred embodiments and techniques. However, it should be understood that many variations and modifications may be made while remaining within the spirit and scope herein.

It is understood that although a number of different embodiments of the catheter systems have been illustrated and described herein, one or more features of any one embodiment can be combined with one or more features of one or more of the other embodiments, provided that such combination satisfies the intent of the present invention.

While a number of exemplary aspects and embodiments of the catheter systems have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope, and no limitations are intended to the details of construction or design herein shown.

What is claimed is:

1. A catheter system for treating a treatment site within or adjacent to a blood vessel or a heart valve within a body of a patient, the catheter system comprising:
   an energy source that generates energy;
   a catheter fluid;
   an emitter assembly including (i) at least a portion of an energy guide having a guide distal end that is selectively positioned near the treatment site, (ii) a plasma generator, and (iii) an emitter housing that is secured to each of the energy guide and the plasma generator to maintain a relative position between the guide distal end of the energy guide and the plasma generator, the energy guide being configured to receive energy from the energy source and direct the energy toward the plasma generator to generate a plasma bubble in the catheter fluid, the plasma generator being configured to direct energy from the plasma bubble toward the treatment site, and the emitter housing including (a) a first housing section that is secured to the energy guide at or near the guide distal end, (b) a second housing section that is secured to the plasma generator, and (c) a connector section that is coupled to and extends between the first housing section and the second housing section; and
   adhesive material that (i) secures the first housing section to the energy guide at or near the guide distal end, and (ii) secures the second housing section to the plasma generator;
   wherein each of the first housing section and the second housing section are substantially cylindrical-shaped; and
   wherein the first housing section includes a housing gap that extends substantially along a length of the first housing section, the first housing section being configured to expand and contract due to changes in environmental conditions.

2. The catheter system of claim 1 wherein the first housing section includes a first housing port positioned between the first housing section and the energy guide, the first housing port being configured to receive the adhesive material so that the adhesive material secures the first housing section to the energy guide at or near the guide distal end.

3. The catheter system of claim 1 wherein the second housing section includes a second housing port positioned between the second housing section and the energy guide, the second housing port being configured to receive the adhesive material so that the adhesive material secures the second housing section to the plasma generator.

4. The catheter system of claim 1 wherein the second housing section includes a housing gap that extends substantially along a length of the second housing section, the second housing section being configured to expand and contract due to changes in environmental conditions.

5. The catheter system of claim 1 further comprising a reinforcement cover that is positioned to substantially encircle the emitter housing.

6. The catheter system of claim 1 further comprising a guidewire lumen that includes an outer surface having a groove, the emitter housing being positioned within the groove.

7. A catheter system for treating a treatment site within or adjacent to a blood vessel or a heart valve within a body of a patient, the catheter system comprising:
   an energy source that generates energy;
   a catheter fluid;
   an emitter assembly including (i) at least a portion of an energy guide having a guide distal end that is selectively positioned near the treatment site, (ii) a plasma generator, and (iii) an emitter housing that is secured to each of the energy guide and the plasma generator to maintain a relative position between the guide distal end of the energy guide and the plasma generator, the energy guide being configured to receive energy from the energy source and direct the energy toward the plasma generator to generate a plasma bubble in the catheter fluid, and the plasma generator being configured to direct energy from the plasma bubble toward the treatment site; and
   a reinforcement cover that is positioned to substantially encircle the emitter housing.

8. The catheter system of claim 7 wherein the first housing section includes a guide aperture, at least a portion of the energy guide being secured within the guide aperture.

9. The catheter system of claim 7 wherein the second housing section includes a generator aperture, at least a portion of the plasma generator being secured within the generator aperture.

10. The catheter system of claim 7 wherein the connector section includes a section opening, the plasma generator being configured to direct the energy from the plasma bubble through the section opening and toward the treatment site.

11. The catheter system of claim 10 wherein the connector section is partially cylindrical-shaped, the section opening extending substantially along a length of the connector section.

12. The catheter system of claim 10 wherein the plasma generator has a proximal end that is angled so that the plasma generator is configured to direct the energy from the plasma bubble through the section opening and toward the treatment site.

13. The catheter system of claim 7 further comprising a balloon including a balloon wall that defines a balloon interior, the balloon being configured to retain the catheter fluid within the balloon interior; wherein the guide distal end, the plasma generator and the emitter housing are positioned within the balloon interior; wherein the balloon is selectively inflatable with the catheter fluid to expand to an inflated state; wherein when the balloon is in the inflated state the balloon wall is configured to be positioned substantially adjacent to the treatment site; and wherein the plasma generator is configured to direct the energy from the plasma bubble toward a portion of the balloon wall that is positioned substantially adjacent to the treatment site.

14. The catheter system of claim 7 wherein the energy guide includes an optical fiber; and wherein the energy source includes a laser.

15. The catheter system of claim 7 wherein the reinforcement cover includes a polyimide tube.

16. A catheter system for treating a treatment site within or adjacent to a blood vessel or a heart valve within a body of a patient, the catheter system comprising:
an energy source that generates energy;
a catheter fluid;
an emitter assembly including (i) at least a portion of an energy guide having a guide distal end that is selectively positioned near the treatment site, (ii) a plasma generator, and (iii) an emitter housing that is secured to each of the energy guide and the plasma generator to maintain a relative position between the guide distal end of the energy guide and the plasma generator, the energy guide being configured to receive energy from the energy source and direct the energy toward the plasma generator to generate a plasma bubble in the catheter fluid, and the plasma generator being configured to direct energy from the plasma bubble toward the treatment site;
a guidewire lumen that includes an outer surface having a groove, the emitter housing being positioned within the groove; and
a reinforcement cover that is positioned to substantially encircle the emitter housing.

17. The catheter system of claim 16 wherein the emitter housing includes (i) a first housing section that is secured to the energy guide at or near the guide distal end, (ii) a second housing section that is one of secured to and integrally formed with the plasma generator, and (iii) a connector section that is coupled to and extends between the first housing section and the second housing section.

18. The catheter system of claim 17 further comprising a first assembly attacher that is positioned adjacent to the first housing section, and a second assembly attacher that is positioned adjacent to the second housing section, the assembly attachers being configured to retain the emitter housing within the groove formed along the outer surface of the guidewire lumen.

19. A catheter system for treating a treatment site within or adjacent to a blood vessel or a heart valve within a body of a patient, the catheter system comprising:
an energy source that generates energy;
a catheter fluid;
an emitter assembly including (i) at least a portion of an energy guide having a guide distal end that is selectively positioned near the treatment site, (ii) a plasma generator, and (iii) an emitter housing that is secured to each of the energy guide and the plasma generator to maintain a relative position between the guide distal end of the energy guide and the plasma generator, the energy guide being configured to receive energy from the energy source and direct the energy toward the plasma generator to generate a plasma bubble in the catheter fluid, and the plasma generator being configured to direct energy from the plasma bubble toward the treatment site; and
a guidewire lumen that includes an outer surface having a groove, the emitter housing being positioned within the groove;
wherein the emitter housing includes (i) a first housing section that is secured to the energy guide at or near the guide distal end, (ii) a second housing section that is one of secured to and integrally formed with the plasma generator, and (iii) a connector section that is coupled to and extends between the first housing section and the second housing section;
wherein the first housing section is substantially cylindrical-shaped; and
wherein the first housing section includes a housing gap that extends substantially along a length of the first housing section, the first housing section being configured to expand and contract due to changes in environmental conditions.

20. The catheter system of claim 19 further comprising a first assembly attacher that is positioned adjacent to the first housing section, and a second assembly attacher that is positioned adjacent to the second housing section, the assembly attachers being configured to retain the emitter housing within the groove formed along the outer surface of the guidewire lumen.

* * * * *